(12) United States Patent
Tennison et al.

(10) Patent No.: US 10,773,234 B2
(45) Date of Patent: Sep. 15, 2020

(54) SHAPED NANOPOROUS BODIES

(71) Applicant: Neoteryx, LLC, Torrance, CA (US)

(72) Inventors: Stephen Robert Tennison, Addlestone (GB); Michal Kowalski, Basingstoke (GB); Thomas Avery, Reading (GB); Susan Rachel Sandeman, Brighton (GB); Carol Angela Howell, Littlehampton (GB); Yishan Zheng, Brighton (GB); Ganesh Ingavle, Brighton (GB); Sergey Victorovich Mikhalovsky, Brighton (GB); Mambet Nuraliyev, Almaty (KZ)

(73) Assignee: Neoteryx, LLC, Torrance, CA (US)

( * ) Notice: Subject to any disclaimer, the term of this patent is extended or adjusted under 35 U.S.C. 154(b) by 139 days.

(21) Appl. No.: 15/745,399

(22) PCT Filed: Jul. 15, 2016

(86) PCT No.: PCT/GB2016/052154
§ 371 (c)(1),
(2) Date: Jan. 16, 2018

(87) PCT Pub. No.: WO2017/009662
PCT Pub. Date: Jan. 19, 2017

(65) Prior Publication Data
US 2019/0022623 A1    Jan. 24, 2019

(30) Foreign Application Priority Data
Jul. 16, 2015   (GB) .................................. 1512468.8

(51) Int. Cl.
*B01J 20/20* (2006.01)
*B01J 20/28* (2006.01)
(Continued)

(52) U.S. Cl.
CPC ............... *B01J 20/20* (2013.01); *A61M 1/34* (2013.01); *A61M 1/3486* (2014.02);
(Continued)

(58) Field of Classification Search
None
See application file for complete search history.

(56) References Cited

U.S. PATENT DOCUMENTS 3,585,104 A   6/1971  Kleinert
5,254,639 A   10/1993 Gardziella et al.
(Continued)

FOREIGN PATENT DOCUMENTS

EP          0254551 B1    6/1994
WO      WO-0212380 A2    2/2002
(Continued)

OTHER PUBLICATIONS

"International Application No. PCT GB2016 052154, International Preliminary Report on Patentability dated Jan. 16, 2018", 10 pgs.
(Continued)

*Primary Examiner* — Monica A Huson
*Assistant Examiner* — Kelsey C Grace
(74) *Attorney, Agent, or Firm* — Schwegman Lundberg & Woessner, P.A.

(57) ABSTRACT

A range of carbon materials can be produced using lignin in combination with synthetic phenolic resins or naturally occurring lingo-cellulosic materials. The lignin, which is essentially a naturally occurring phenolic resin, has a carbon yield on pyrolysis similar to that of the synthetic resins, which aids processing. The lignin can be used as a binder phase for synthetic resin or lignocellulosic materials allowing the production of monolithic carbons from a wide range of precursors, as the primary structural material where the
(Continued)

Monolith channel structure

Wall Structure – macro-particles

Macro-particle structure, micro-domains thermal processing is modified by the addition of small quantities of synthetic resin materials or as structure modified in the production of meso/macro porous carbons in either bead, granular or monolithic form. A carbonised monolith is provided comprising mesoporous and/or macroporous carbon particles dispersed in a matrix of microporous carbon particles with voids between the particles defining paths for fluid to flow into and through the structure. The monolith may take the form of a shaped body having walls defining a multiplicity of internal transport channels for fluid flow, the transport channels being directed along the extrusion direction. The monolith may be made by carbonising a shaped phenolic body based on phenolic resin precursors. In a method for producing such a carbonisable shaped resin body solid particles of a first phenolic resin are provided which is partially cured so that the particles are sinterable but do not melt on carbonisation. The particles of the first phenolic resin are mixed with particles of a second phenolic resin that has a greater degree of cure than said first phenolic resin and has a mesoporous and/or macroporous microstructure that is preserved on carbonisation. The resulting mixture is formed into a dough e.g. by mixing the resin particles with methyl cellulose, PEO and water, after which the dough is extruded to form a shaped product and stabilising in its shape by sintering.

6 Claims, 19 Drawing Sheets

(51) Int. Cl.
*C01B 32/354* (2017.01)
*A61M 1/34* (2006.01)
*A61M 1/36* (2006.01)
*B01J 20/30* (2006.01)

(52) U.S. Cl.
CPC ...... *A61M 1/3679* (2013.01); *B01J 20/28042* (2013.01); *B01J 20/28045* (2013.01); *B01J 20/28078* (2013.01); *B01J 20/28083* (2013.01); *B01J 20/28085* (2013.01); *B01J 20/3007* (2013.01); *B01J 20/3021* (2013.01); *B01J 20/3064* (2013.01); *B01J 20/3078* (2013.01); *C01B 32/382* (2017.08); *B01J 2220/485* (2013.01); *B01J 2220/4875* (2013.01); *C01P 2006/17* (2013.01)

(56) References Cited

U.S. PATENT DOCUMENTS

| | | | |
|---|---|---|---|
| 5,750,026 | A | 5/1998 | Gadkaree et al. |
| 6,964,695 | B2 | 11/2005 | Place et al. |
| 8,383,703 | B2 | 2/2013 | Tennison et al. |
| 2002/0150686 | A1 | 10/2002 | Mitchell et al. |
| 2004/0045438 | A1 | 3/2004 | Place et al. |
| 2008/0025907 | A1 | 1/2008 | Tennison et al. |
| 2010/0298134 | A1 | 11/2010 | De Leede et al. |
| 2013/0072845 | A1 | 3/2013 | Tennison et al. |
| 2015/0090157 | A1* | 4/2015 | Sniady .................. C08L 97/02 106/164.4 |

FOREIGN PATENT DOCUMENTS

| | | |
|---|---|---|
| WO | WO-02072240 A2 | 9/2002 |
| WO | WO-02083559 A1 | 10/2002 |
| WO | WO-2004087612 A1 | 10/2004 |

OTHER PUBLICATIONS

"International Application Serial No. PCT/GB2016/052154, International Search Report and Written Opinion dated Nov. 14, 2016", 15 pgs.

Sandeman, S. et al., "Characterising Nanoporous Carbon Adsorbents for Biological Application to Chronic Kidney Disease", Journal of Biomaterials and Tissue Engineering. American Scientific Publ. US. vol. 2. No. 1, (Mar. 31, 2012), 40-47.

* cited by examiner

Figure 1 Monolithic Structure
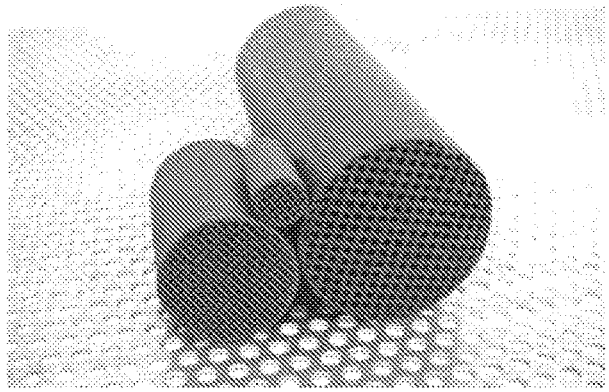
Figure 2 Structure of Carbon Monoliths
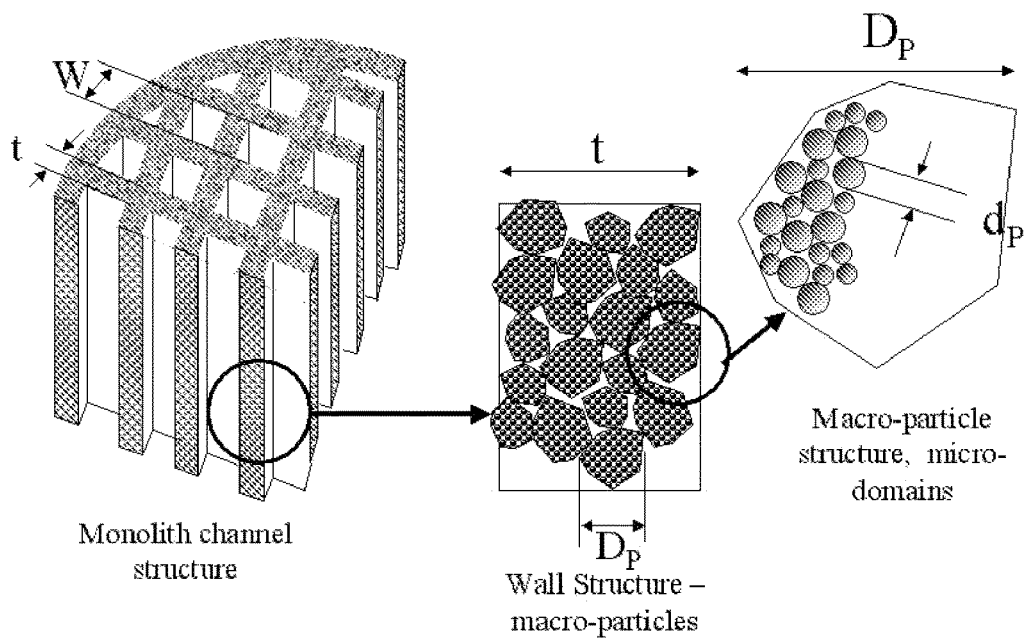
Figure 3 Composition of Lignocelluloses as Function of the Precursor

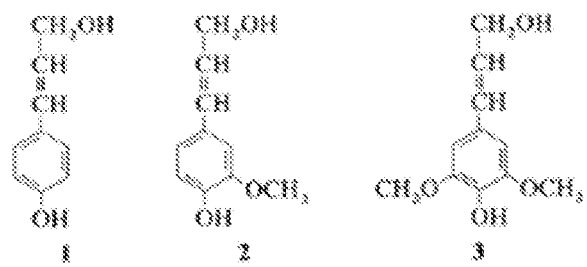
Figure 4A Primary Lignin Components P-coumaryl-, coniferyl- and sinapyl alcohols: dominant building blocks of the amorphous lignin polymer.
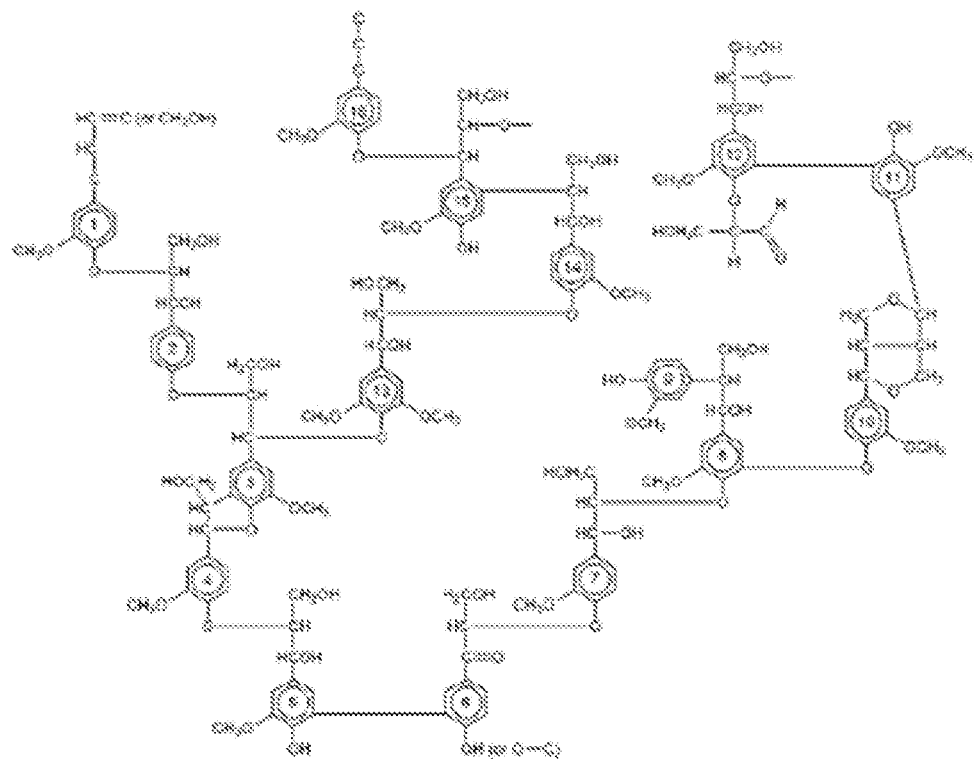
Figure 4B Model Structure of Spruce Derived Lignin

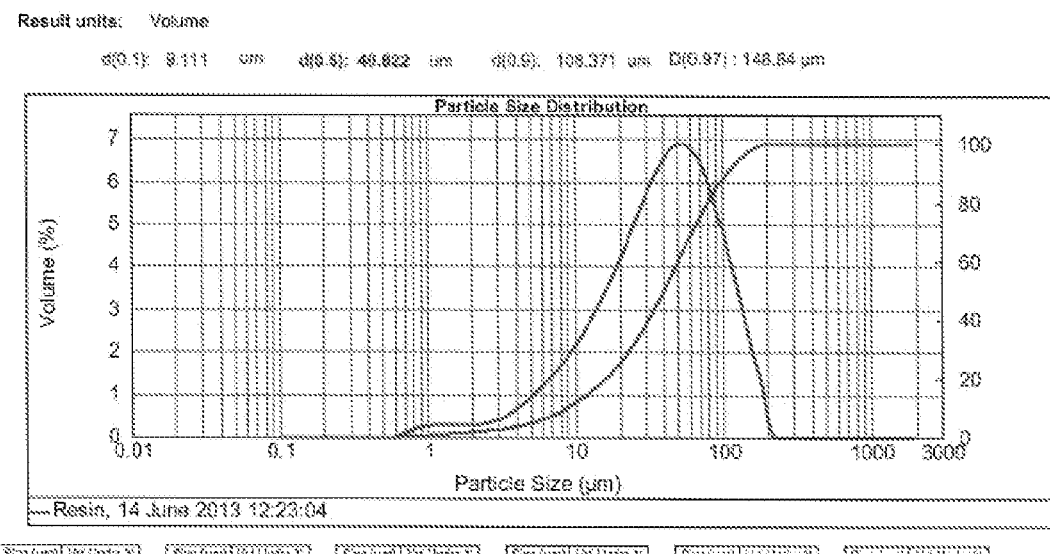
Figure 5 Particle Size Distribution of Jet Milled Resin
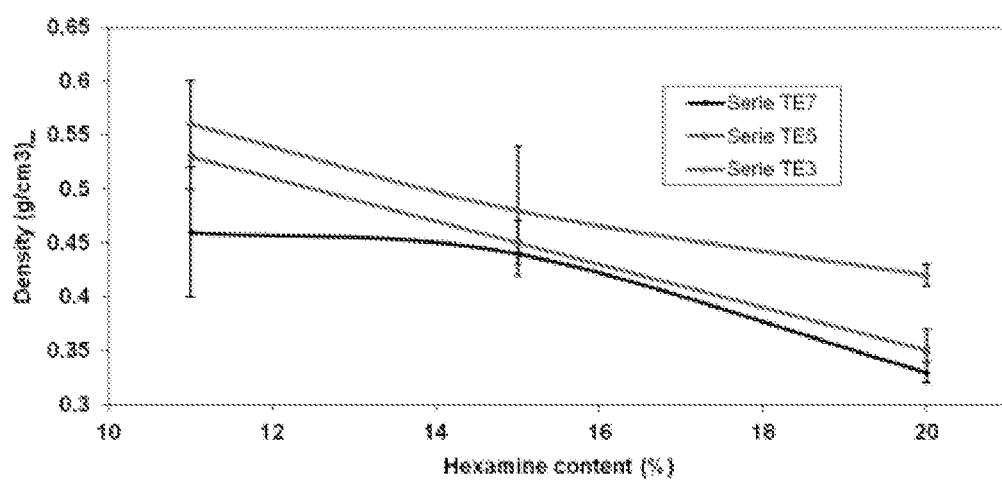
Figure 6 Density as a function of pore former and HMTA content

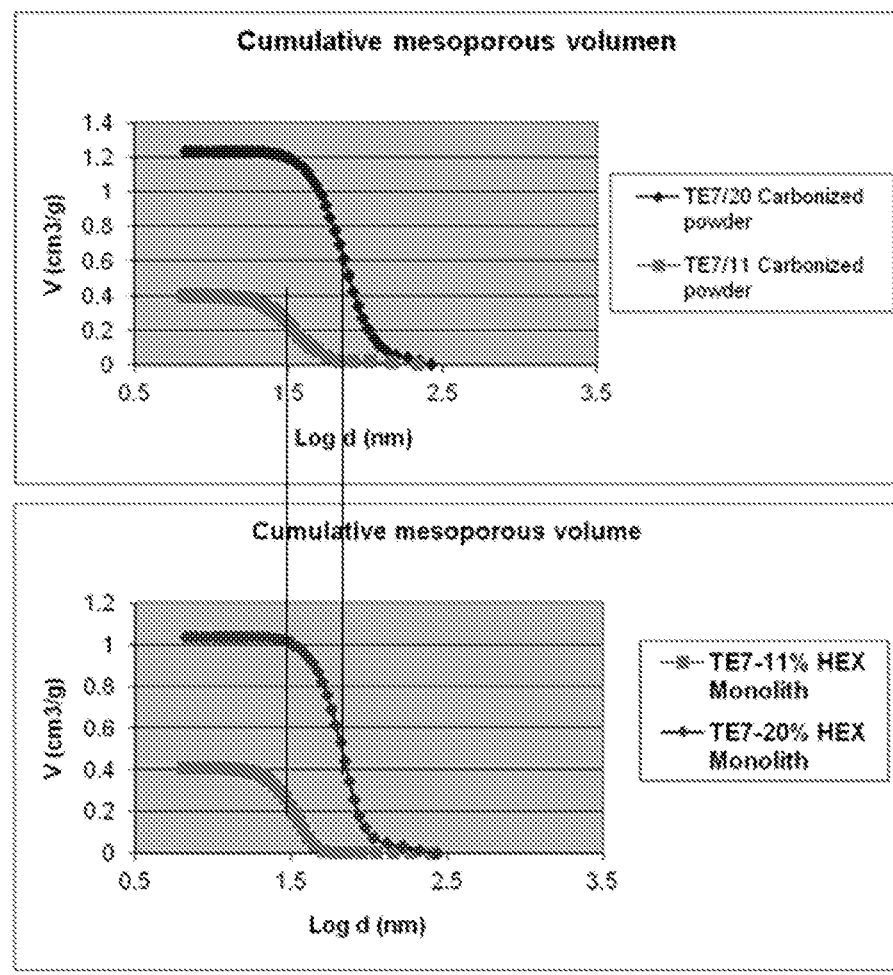
Figure 7 Variation in Mercury Pore volume with HMTA content for macroporous (TE7) powder and monoliths.
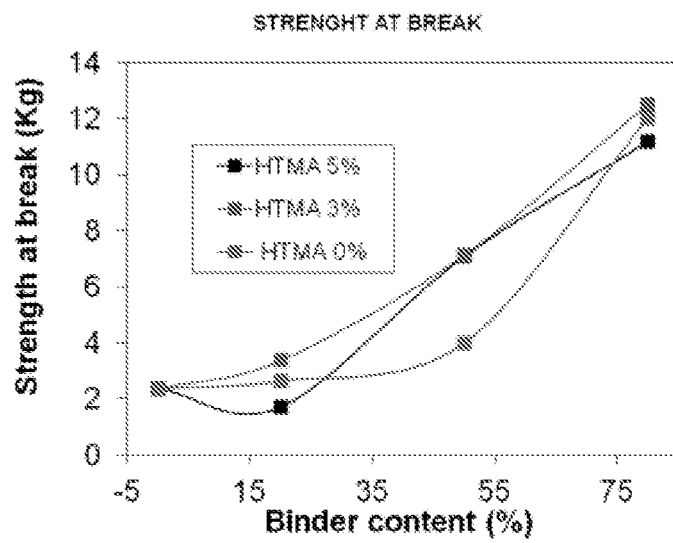
Figure 8 Effect of Novolac Cure and loading on Extrudate Strength

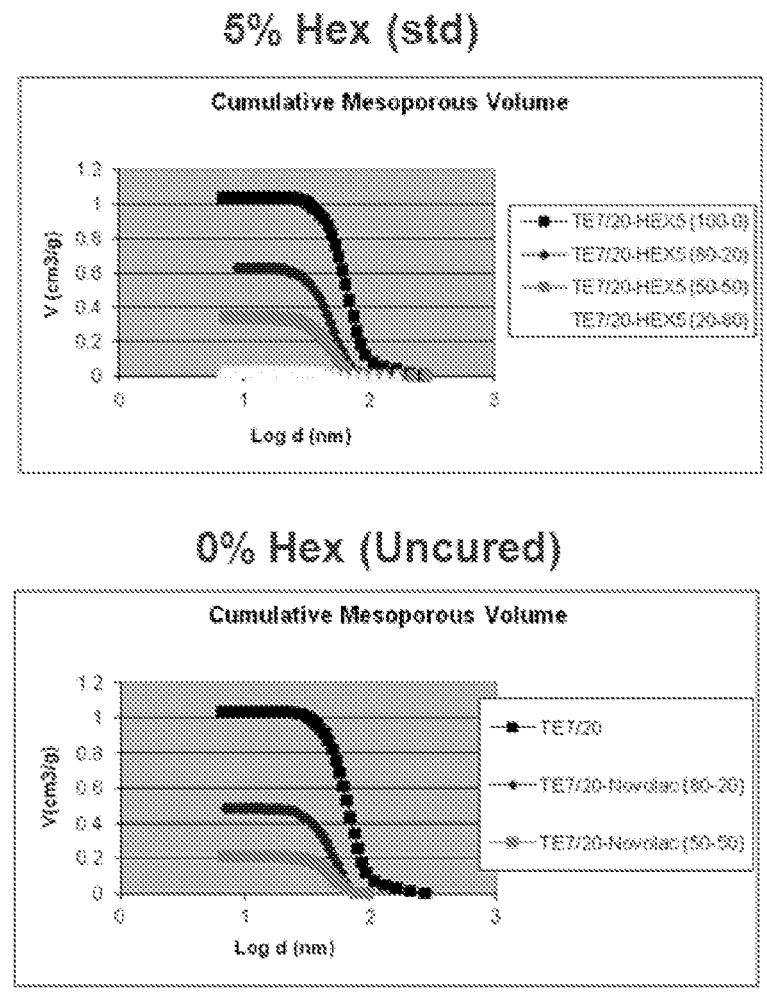
Figure 9 Effect of Binder Resin Curing on Pore Structure of Carbon Rods
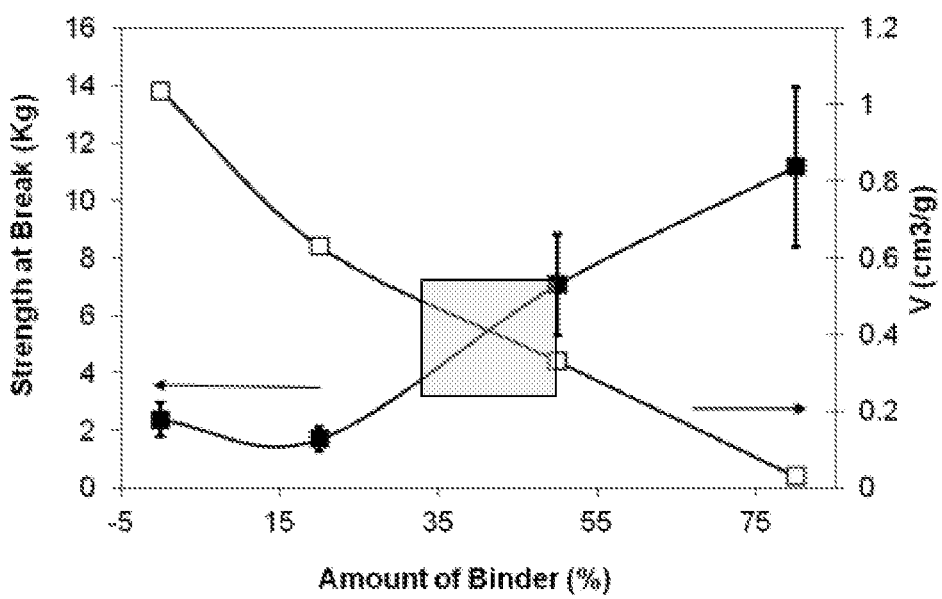
Figure 10 Comparison of strength and porosity as a function of binder resin concentration

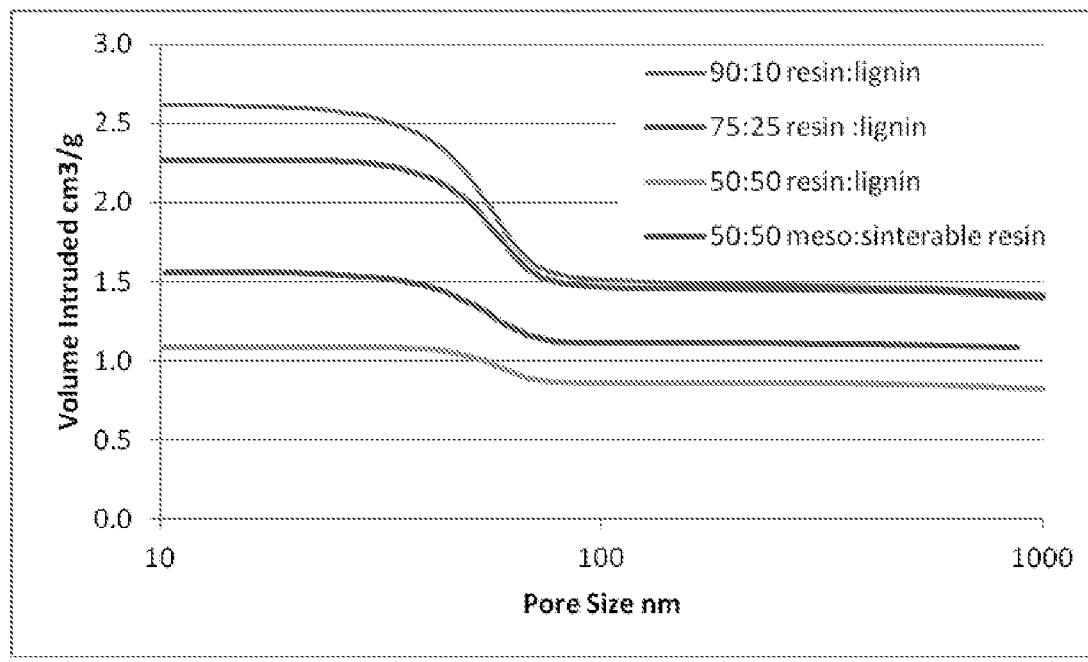
Figure 11 Mercury Intrusion for Lignin bound mesoporous resins
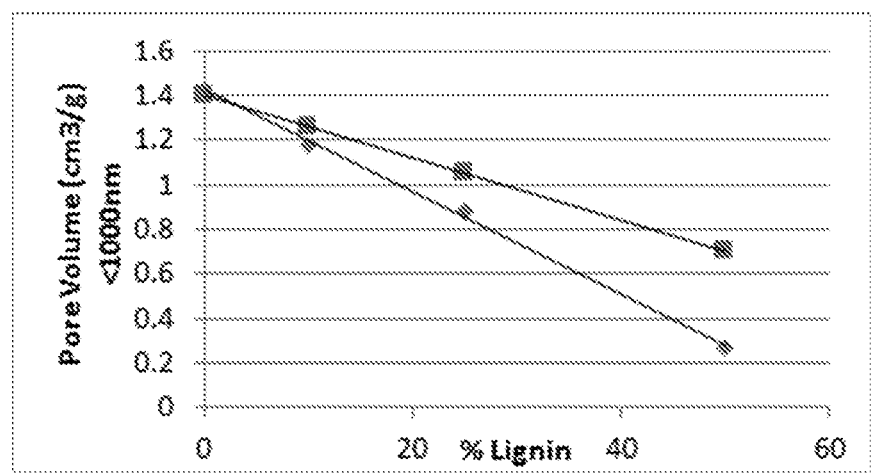
Figure 12 Loss in Pore Volume with Lignin Binder

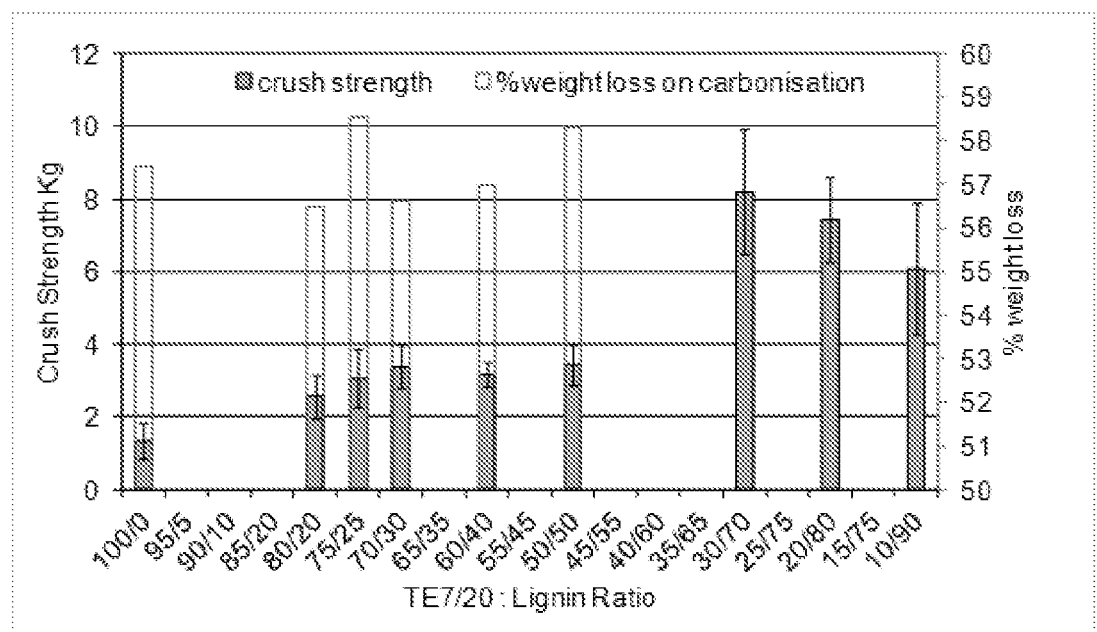
Figure 13  Weight loss and Crush Strength for TE7/20 - Lignin composite extrudates
Figure 14  100% lignin monolith after pyrolysis Figure 15  Meso-macro pore size distribution of ethylene glycol modified J1098F
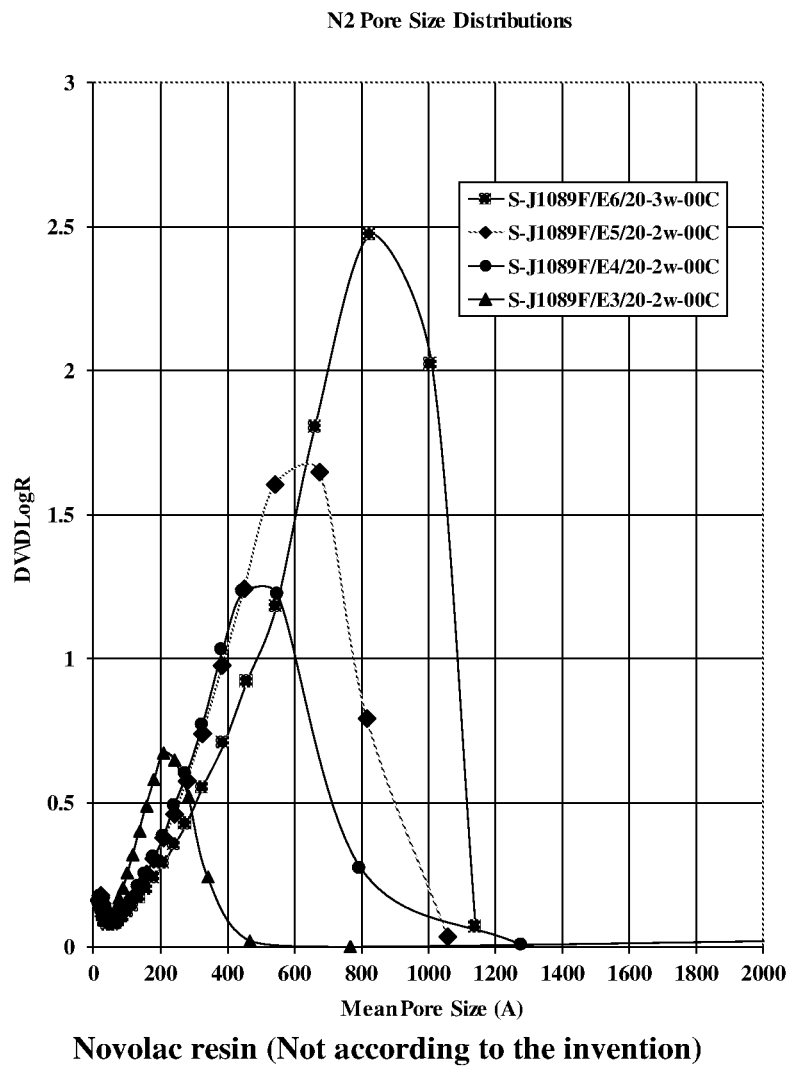
Novolac resin (Not according to the invention)

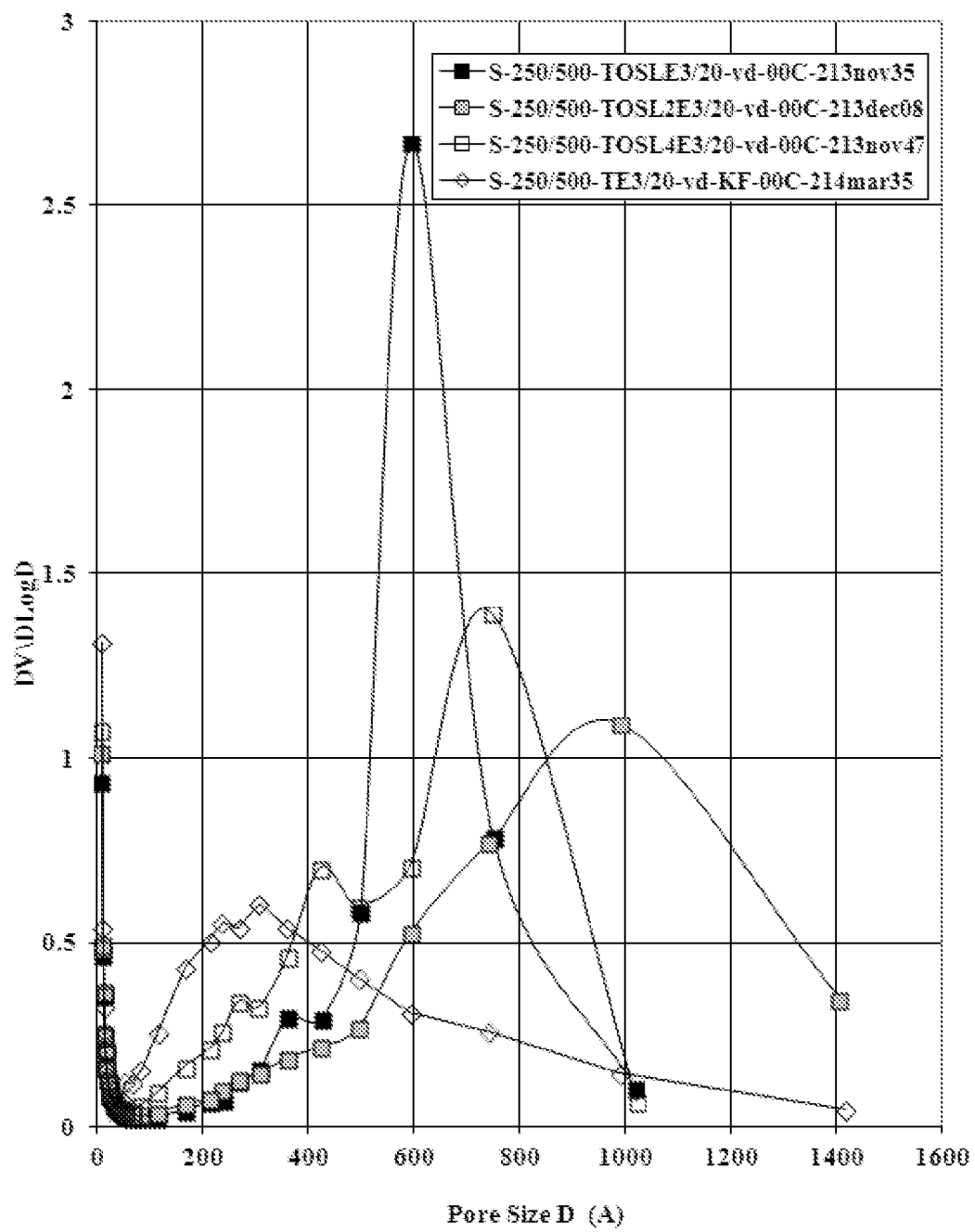
Figure 16 Pore Size Distribution as a Function of OSL content

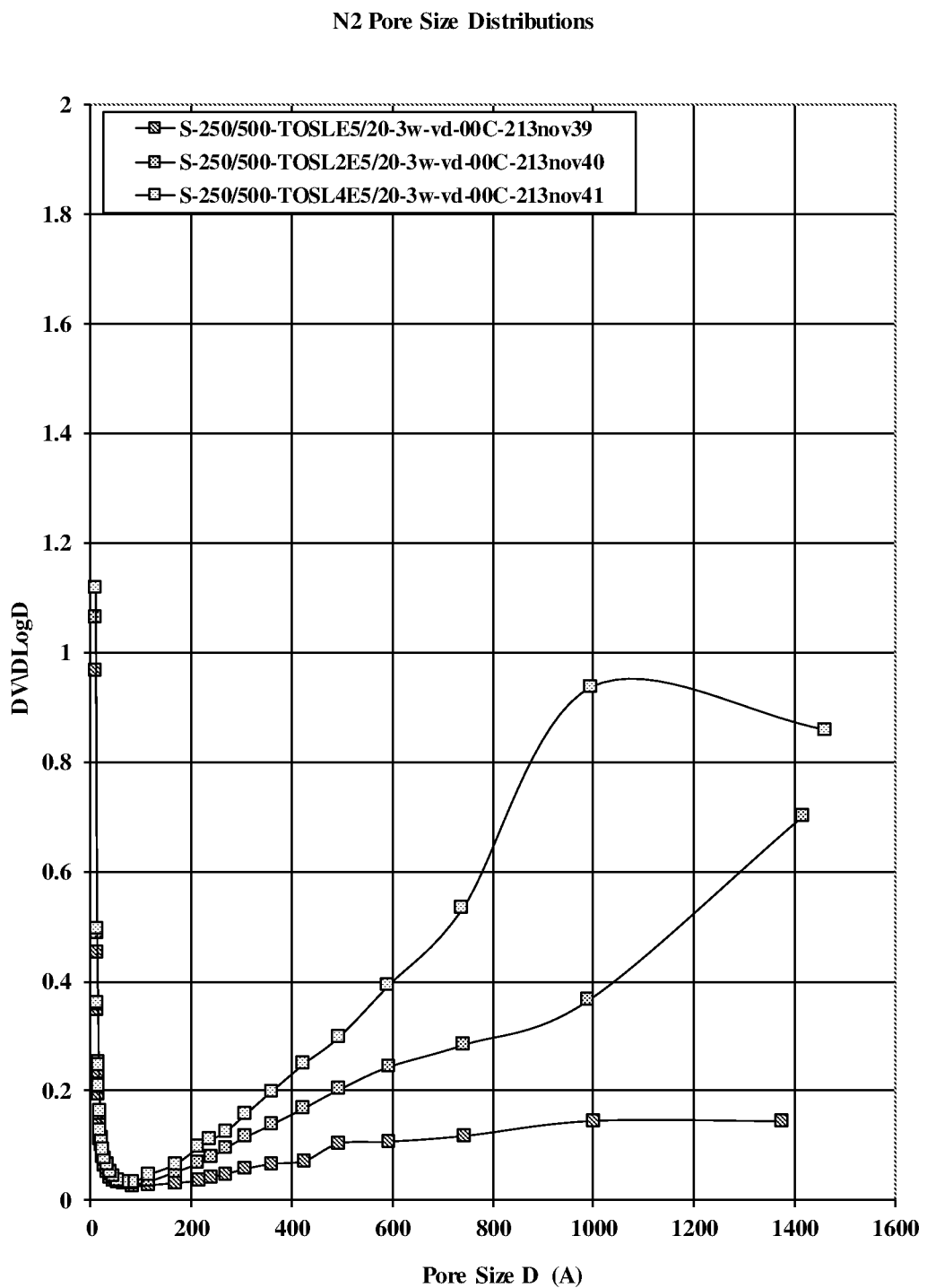
Figure 17 Pore Size Distribution of E5 Resin-OSL composite beads

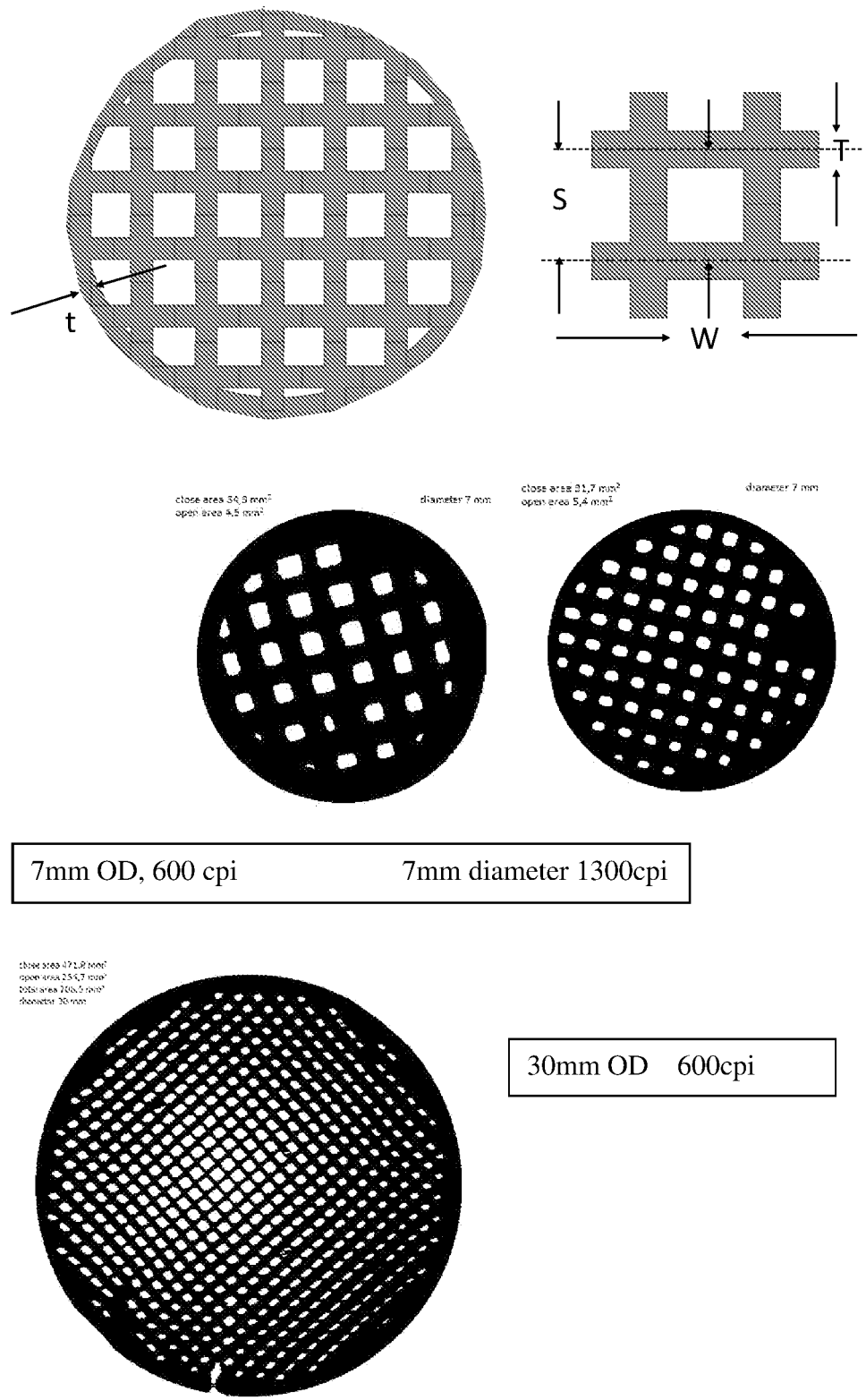
Figure 18 Monolith Geometry

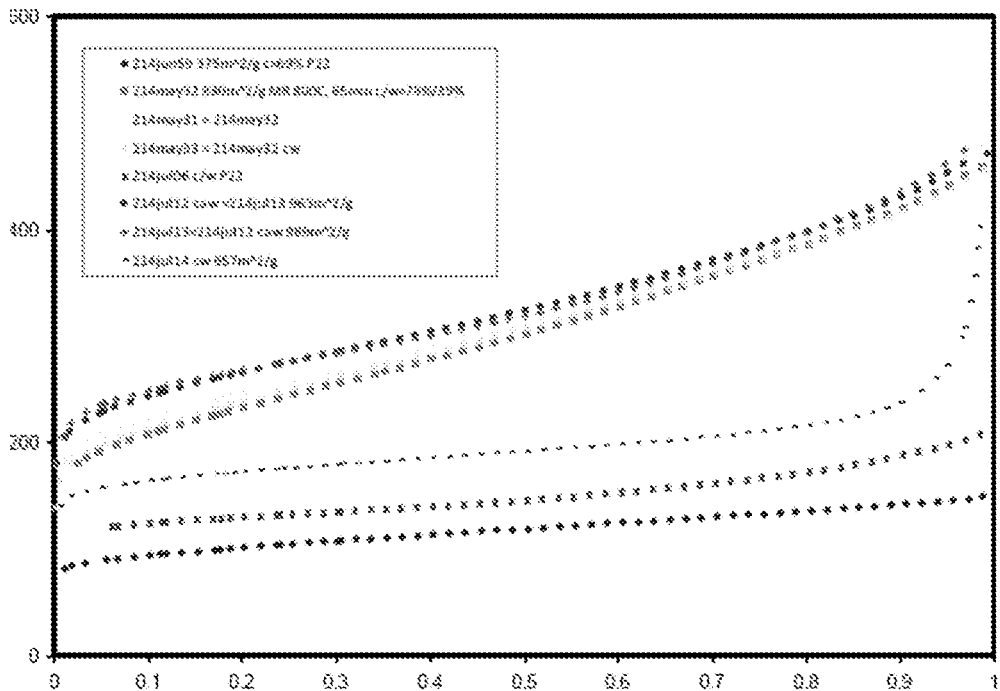
Figure 19 Adsorption Isotherms for Various Rice Husk based Monoliths - Volume $N_2$ adsorbed ($cm^3/g$) vs $P/P_0$ Nitrogen.
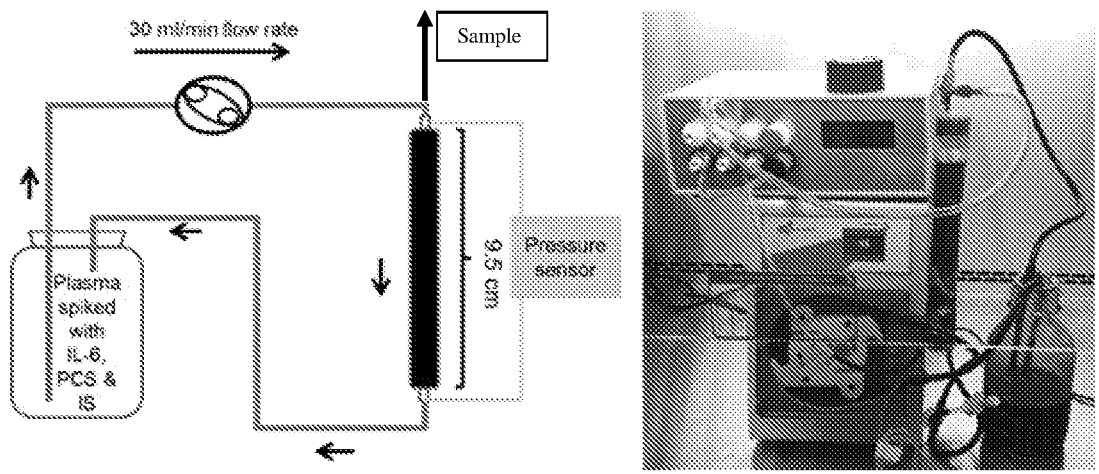
Figure 20 Flow Diagram for Monolith Test Facility, samples being taken from the tube entering the blood/plasma reservoir

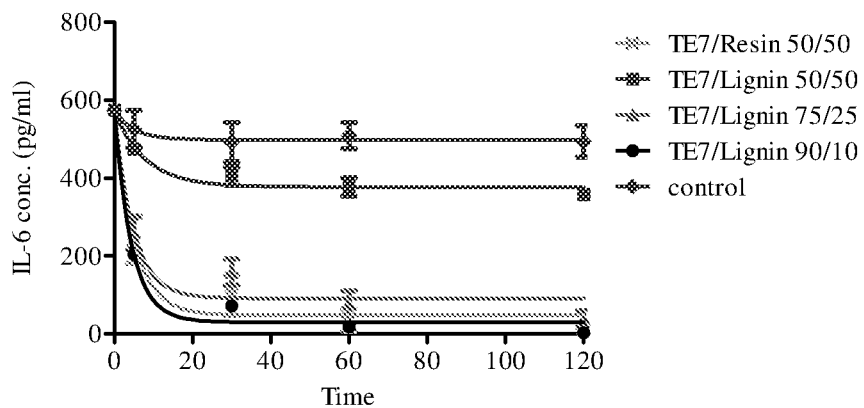
Figure 21 IL-6 Removal using lignin bound monoliths
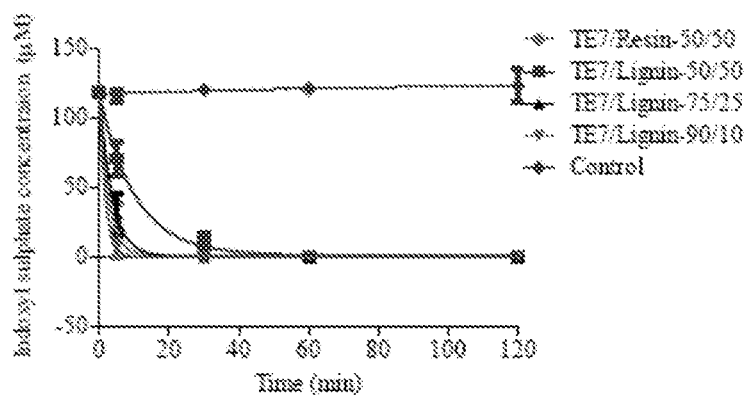
Figure 22 Removal of IS Using Lignin Bound Monoliths. IS remaining in the plasma sample after 5, 30, 60 and 120 minutes of circulation through tested AC monoliths: TE7/Lignin (90-10) (green), TE7/Lignin (75-25) (black), TE7/Micro (50-50) (red) and TE7/Lignin (50-50) (blue). A control (purple) was also included as a reference (SEM ± n=3).

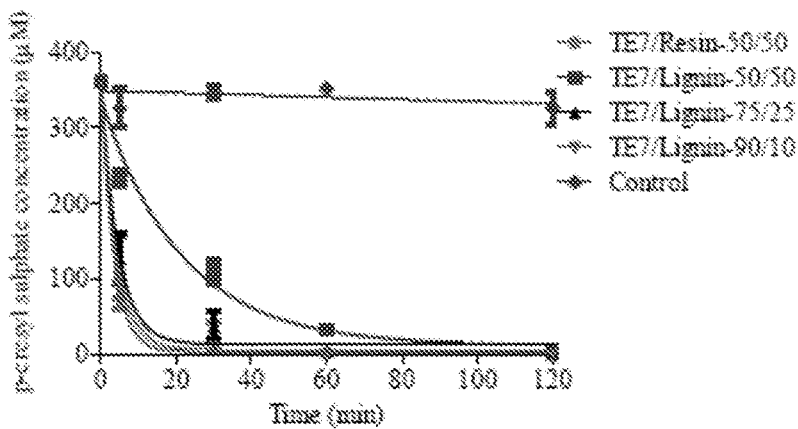

Figure 23 PCS remaining in the plasma sample after 5, 30, 60 and 120 minutes of circulation through monoliths: TE7/Lignin (90-10) (green), TE7/Lignin (75-25) (black), TE7/Micro (50-50) (red) and TE7/Lignin (50-50) (blue). A control (purple) was also included as a reference (SEM ± n=3).

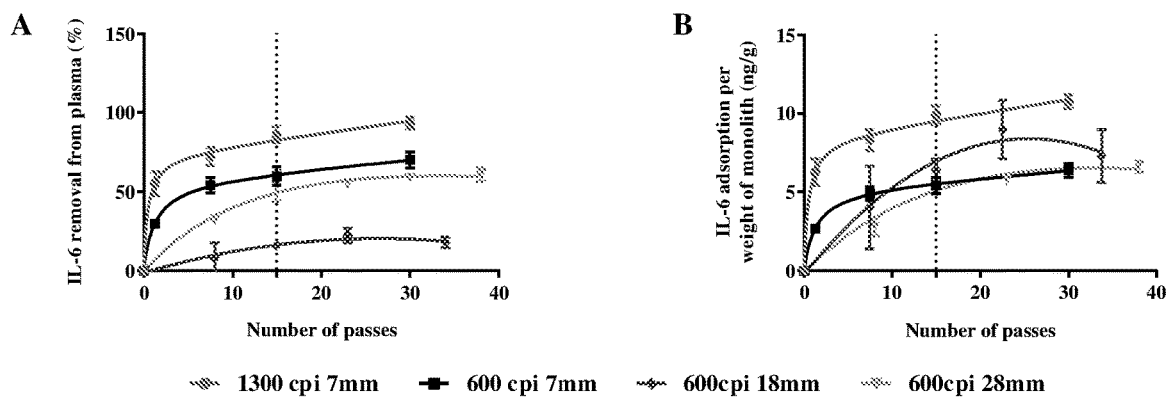

Figure 24 The removal of spiked cytokine marker IL-6 from human plasma pool by carbon monoliths. (A) the IL-6 removal expressed as percentage of IL-6 concentration at time 0; (B) the removal of IL-6 is expressed as ng of IL-6 adsorbed by each gram of activated carbon

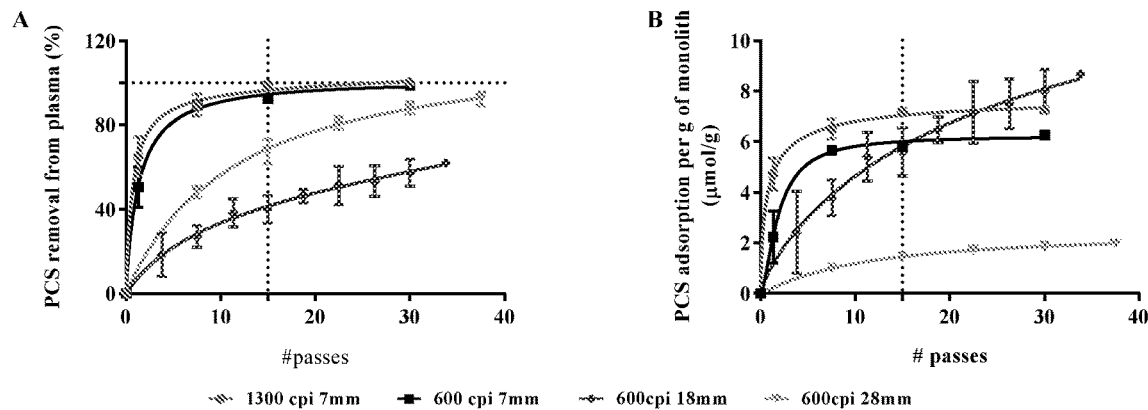

Figure 25 The removal of spiked albumin bound uraemic toxin marker p-cresyl sulphate (PCS) from human plasma pool by carbon monoliths. (A) the percentage of PCS removed; (B) the amount of PCS (μmol) adsorbed by each gram of activated carbon

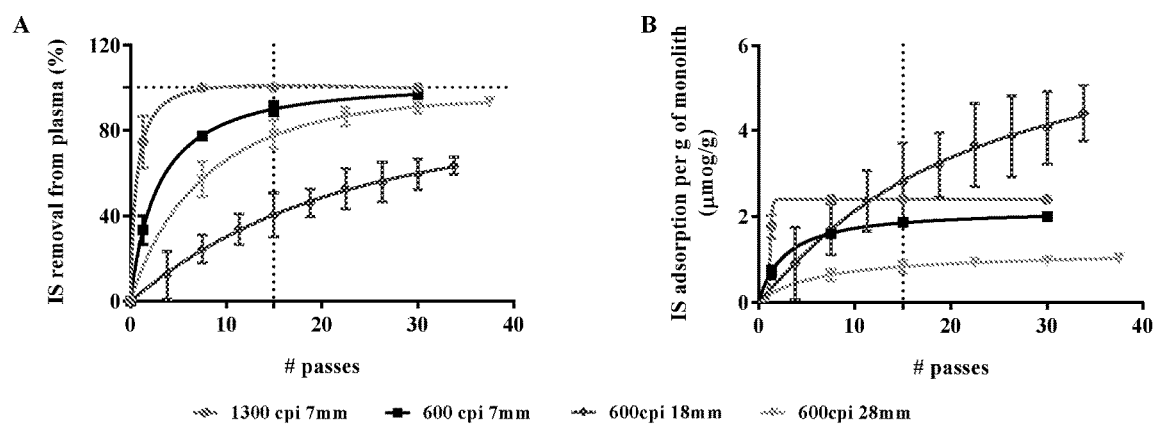

Figure 26 The removal of spiked albumin bound uraemic toxin marker indoxyl sulphate (IS) from human plasma pool by carbon monoliths. (A) the percentage of IS removed; (B) the amount of IS (μmol) adsorbed by each gram of activated carbon.

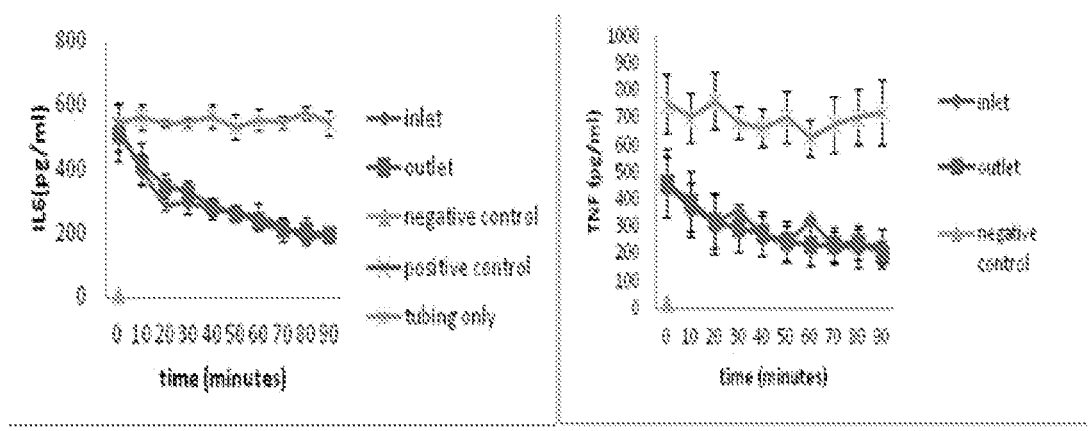
Figure 27 adsorption of IL-6 and TNF from plasma in 30mm diameter lignin bound monoliths
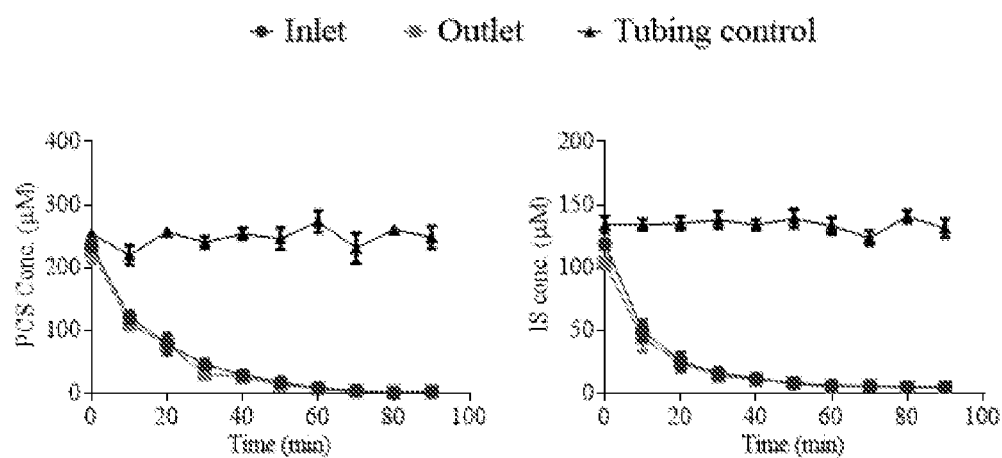
Figure 28 adsorption of PCS and IS from circulating plasma using 30mm lignin bound monoliths Figure 29 adsorption of PCS, IS, IL-6 and TNFα from whole blood using 30 mm monoliths Figure 30 adsorption of Staphylococcal enterotoxin B (SEB) from human plasma using carbon beads with 1nm pores (carbon 1), 30nm pores (Carbon 5) and 100nm pores (carbon 9)

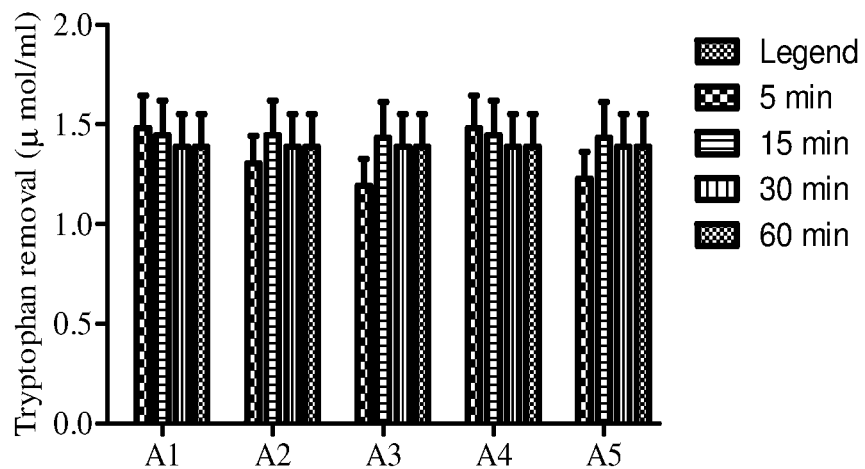

Figure 31 Amount of tryptophan removed from the spiked human plasma. Samples were collected after the 0.6 ml of AC beads (A-1, A-2, A-3, A-4 and A-5) incubated with 5.4 ml of tryptophan (0.1 µmol/ml) spiked fresh frozen human plasma for 5, 15, 30 and 60 min, and analysed using HPLC. Tryptophan removal was calculated based on the volume of the AC beads. (Mean n=4, ± SEM)

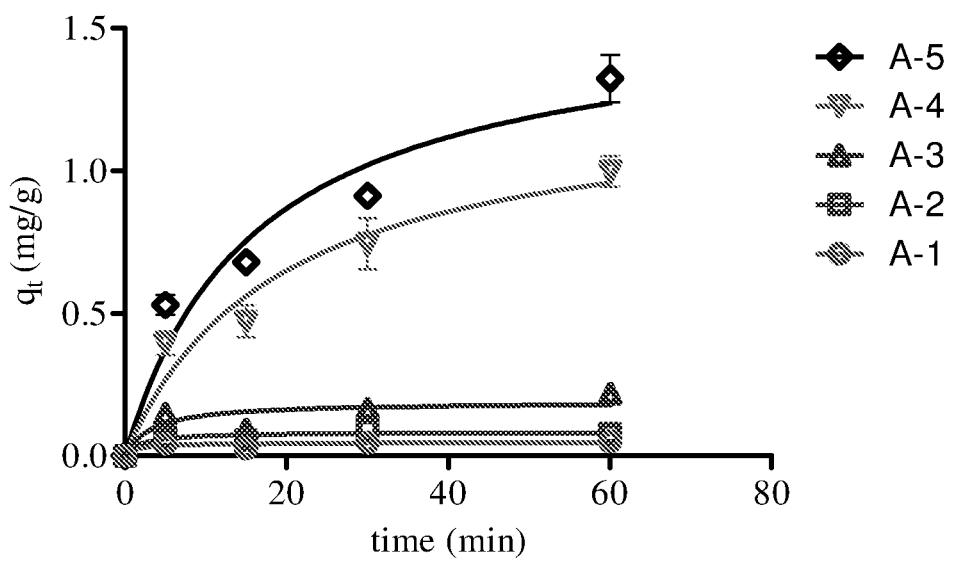

Figure 32 Adsorption kinetics of bilirubin by AC1-5 from spiked plasma. The adsorption kinetics of bilirubin by 0.4 ml microporous carbon (A1), mesoporous carbon (A2) and macroporous carbon (A3, A4 and A5) from 5.6 ml 300 µM bilirubin spiked plasma was observed at 4 time points over 60 min of incubation period. (Mean n=5, ± SEM)

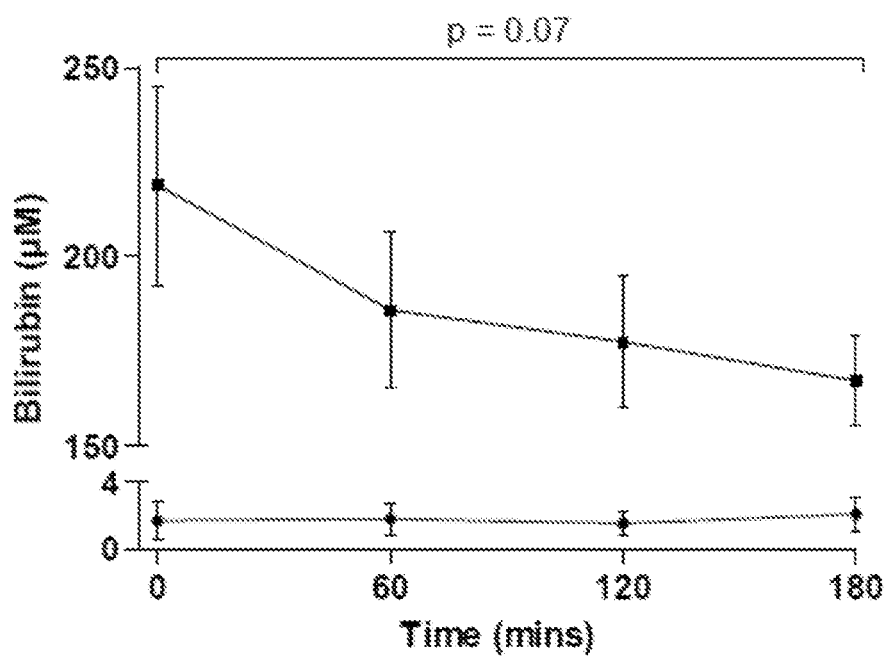
Figure 33 Reduction in Bilirubin content of circulating blood of a bile duct ligation (BDL) animal model of liver failure during haemoperfusion using macroporous carbon monolith (upper line) and sham control (lower line)

SHAPED NANOPOROUS BODIES

CLAIM OF PRIORITY

This application is a U.S. National Stage Filing under 35 U.S.C. 371 from International Application No. PCT/GB2016/052154, filed on Jul. 15, 2016, and published as WO 2017/009662 A1 on Jan. 19, 2017, which claims the benefit of priority under 35 U.S.C. § 119 to United Kingdom Patent Application No. 1512468.8, filed on Jul. 16, 2015, each of which is hereby incorporated by reference herein in its entirety.

FIELD OF THE INVENTION

This invention relates to a method for producing complex shaped nanoporous materials through the use of lignin as a binder for pyrolysable precursors.

BACKGROUND TO THE INVENTION

Known methods for the production of complex shaped controlled porosity adsorbent material are discussed in WO 2004/087612 (Blackburn and Tennison, the disclosure of which is incorporated herein by reference). The inventors explain that there are very few viable routes for the production of complex shaped controlled porosity adsorbent materials. For instance, they explain that activated carbon is traditionally produced by taking a char made by pyrolysing an organic precursor or coal, grinding the char to a fine powder, mixing this with a binder, typically pitch, and extruding or pressing to give a "green" body. The green body is then further fired to pyrolyse the binder and this is then typically further activated in steam, air, carbon dioxide or mixtures of these gases to give the high surface activated carbon product. The drawback to this route is that the binder, which is usually a thermoplastic material, goes through a melting transition prior to pyrolytic decomposition. At this point the material is weak and unable to support a complex form. This, combined with the problems of activating the fired body, typically limits the size and shape of the products to simple extrudates.

An alternative route is to take an activated carbon powder and form this directly into the final shape. In this instance a range of polymeric binders have been used that remain in the final product. The main drawback to this route is that high levels of binders are required and these then tend to both fill the pores of the activated carbon powder and encapsulate the powder, leading to a marked reduction in adsorption capacity and a deterioration in the adsorption kinetics. The presence of the polymeric phase also degrades the physical and chemical stability of the formed material, severely limiting the range of applicability.

A further alternative is to take a formed ceramic material, such as a multichannel monolith, and to coat this with a carbon forming precursor such as a phenolic resin. It can then be fired and activated to produce a ceramic-carbon composite. The main limitations of this route are the cost associated with the ceramic substrate and the relatively low volume loading of carbon. At high degrees of activation it is possible to produce a mesoporous carbon although the carbon volumetric loading and the mechanical stability of the carbon is further reduced.

The applicants have previously developed methods for making carbonised and optionally activated monoliths from phenolic resin precursors. Monolithic porous carbon can be made by partially curing a phenolic resin to a solid, comminuting the partially cured resin, extruding the comminuted resin, sintering the extruded resin so as to produce a form-stable sintered product and carbonising and activating the form-stable sintered product. EP 0 254 551 (Satchell et al., the contents of which are incorporated herein by reference) gives details of methods of forming porous resin structures suitable for conversion to porous carbon structures. WO 02/072240 (Place et al . . . the disclosure of which is incorporated herein by reference) gives further details of producing monolithic structures using sintered resin structures of EP 0 254 551.

In this process for producing carbon monoliths, the resin cure is controlled so that it is sufficient to prevent the resin melting during subsequent carbonisation but low enough that the resin particles produced during the milling step can sinter during subsequent processing. The amount of cross-linking agent and the temperature and duration of the partial curing step are selected as to give a degree of cure sufficient to give a sinterable product, and such that a sample of the partially cured solid when ground to produce particles in the size range 106-250 µm and tabletted in a tabletting machine gives a pellet with a crush strength which is not less than 1 N/mm. Preferably the pellet after carbonisation has a crush strength of not less than 8 N/mm.

The comminuted resin particles may have a particle size of 1-250 µm, in embodiments 10-70 µm. In further embodiments the resin powder size is 20-50 µm which provides for inter-particle channels of size of 4-10 µm with an inter-particle channel volume of 30-40%. The size of the particles is selected to provide a balance between diffusivity through the inter-particle voids and within the particles.

As disclosed in U.S. Pat. No. 6,964,695 (Place et al., Carbon Technologies) the milled powder can then be extruded to produce polymeric monolithic structures with a wide range of cell structures, limited only by the ability to produce the required extrusion die, or other forms such as rods, tubes, trilobes etc. Suitable dies are well known to those skilled in the art. At this stage the monolith has a bimodal structure—the visible channel structure with either the central channel in a simple tube or the open cells in a square channel monolith of typically 100-1000 µm cell dimension and cell walls with thickness typically 100-1000 µm and the inter-particle void structure within the walls generated by the sintered resin particles.

Carbonisation takes place preferably by heating above 600° C. for the requisite time e.g. 1 to 48 hours and takes place under an inert atmosphere or vacuum to prevent oxidation of the carbon. On carbonisation the material loses about 50% weight and shrinks by about 50% volume but, provided the resin cure stage was correctly carried out, this shrinkage is accommodated with little or no distortion of the monolith leading to a physical structure identical to that of the resin precursor but with dimensions reduced by ~30%. The inter-particle void size is also reduced by ~30% although the void volume (ml/ml) remains essentially unaltered. During carbonisation the microstructure of the porous carbon develops, particularly at temperatures above 600° C. After carbonisation there may be partial blocking of the microstructure by the decomposition products from the carbonisation process. These blockages may be removed by activation to provide rapid access to the internal structure of the carbon that may be desirable for the operation of the monoliths as adsorption devices.

This production route is limited to the use of Novolac resins and this in turn limits the pore structure that can be produced to the approximately 1 nm pores that are characteristic of all novolac derived carbons and larger macropores, typically greater than 1 µm, that are produced by the voids between the sintered particles. It is not possible by this route to produce products with pores in the large meso-small micro range of sizes.

In US 2013/0072845 (Tennison et al.) a method is described for extending the porosity of the above structures to include meso and or small macro pores in addition to the micropores that derive from the novolac resin. In this invention solid particles of a first phenolic resin which is partially cured so that the particles are sinterable but do not melt on carbonisation are mixed with particles of a second phenolic resin that has a greater degree of cure than said first phenolic resin and has a mesoporous and/or macroporous microstructure generated by solvent pore forming that is preserved on carbonisation; forming the mixture into a dough; extruding the dough to form a shaped product and stabilizing its shape by sintering.

In the above method, the dough may be extruded to form a shaped body having walls defining a multiplicity of internal channels for fluid flow, the channels being directed along the extrusion direction e.g. as discussed in relation to FIG. 1. There may further be carried out the step of carbonising the resin, and optionally activating the carbonised resin.

In this production route the secondary, highly cured, meso/macro porous resin component is not strongly bound into the structure due to its high degree of cure but rather is trapped in a cage formed by the sinterable resin component. This approach limits the amount of the second material than can be incorporated due to the requirement to form the cage structure. This leads to a reduction in strength when compared to the materials produced entirely from the sinterable resin particles. The extent of the larger pore structure is also limited by dilution of the matrix with the first resin component. This production route can also be used with second components other than phenolic resin such as activated carbons but in this instance differential shrinkage between the particles comprising the cage and the second component during the pyrolysis process leads to stress cracking and a further reduction in mechanical strength. Thus whilst it is possible to produce complex shapes the reduced meso/macro pore capacity and strength limits there used in demanding applications such as blood filtration.

The production of the large meso/small micro pore carbons is described in U.S. Pat. No. 8,383,703 (Tennison et al., 2103) which is incorporated herein by reference. The preferred route for producing these materials is through the use of pore formers where ethylene glycol is the preferred component although other solvents may also be used. These meso/macro porous resins can be produced either as beads or as powders. In the routes described in US 2008/025907 (Tennison et al.) the precursors, typically comprising the novolac resin and the curing agent (typically hexamethylenetetramine (HTMA)) are dissolved in the pore forming solvent (typically ethylene glycol) in the ratios necessary to generate the required pore structure and degree of cure. The mixture can either be cured by dispersing in hot oil to form beads or placed in trays and cured in an oven. In the latter case the block of cured resin is subsequently processed by milling to give either the finished powder or a precursor for extrusion. The limitation of this route is the strength, attrition resistance and control of porosity in monolith materials produced by this route is insufficient to allow these materials to be used in demanding applications such as blood filtration.

There is therefore a requirement for a production route that permits the production of complex shaped nanoporous carbons with multimodal pore structures with sufficient strength and attrition resistance to allow their use in applications such as haemofiltration

SUMMARY OF THE INVENTION

One problem with which the invention is concerned is how to bind these highly cured porous resins, or other materials, into the structure to give a high strength, attrition-resistant structure.

We have now surprisingly found that lignin, which is essentially a naturally occurring phenolic resin, can be used as a binder phase with a wide range of second phases. In marked contrast to the problems experienced when using pitch as a binder, as is normally used in commercial activated carbon processes, the use of lignin produces form-stable green materials which show little or no distortion on firing. We have now found that in marked contrast to the tars or pitches normally used as binders in active carbon production, lignins can be used as binders for a wide range of nanoporous precursors, significantly expanding the range of controlled structure materials that can be produced. Without being bound by this explanation we believe that the viscosity, melt flow and carbonisation characteristics of the lignins allows them to bond the second phase particles together without excessive flow which would infiltrate the pore structure of the second phase and would also disperse throughout the matrix giving poor bonding. These materials then convert to carbon with a high yield of typically around 30% without the addition of any curing agents.

We have found these lignin binders can be beneficially used with a wide variety of second phases including but not limited to:
 controlled meso/macro structure phenolic resins,
 phosphoric acid activated micro/meso porous carbon powders,
 activated carbon powders and
 porous inorganic materials such as silicas, zeolites etc.

However, the route is particularly beneficial for polymeric (e.g. phenolic resins) or other biological precursors, for example waste organic materials such as hemp shives, flax waste, rice husks or any other lignocellulose derived material. In this case this is because the shrinkage of the natural precursor is similar to or greater than that of the lignin binder allowing carbonisation without the stress cracking associated with the use of inorganic materials.

The lignins have the further advantage that, as essentially naturally occurring phenolic resins, they are compatible and co-soluble with the novolac resins used in the formation of other phenolic resin derived carbons. They cannot be cross-linked in the same way as novolac resins which means that in their pure form they cannot be easily converted to controlled meso-macro pore structure carbons as they melt and foam during pyrolysis. However we have surprisingly found that when processed as a mixture with a standard Novolac resin, or a natural precursor, the melting characteristics of the lignin are suppressed allowing the production of complex shaped and pore structure products, even with very low levels of the second phase material.

The lignin can also be stabilised by controlled oxidation. It is then possible for instance to make a monolithic structure from a pure lignin precursor. In this instance the lignin powder can be extruded as described above for the cured phenolic resin powder. After drying the monoliths are then placed in an air oven at ~300° C. overnight. The monolith can then be pyrolysed as normal without the melt flow characteristic exhibited by the feed resin powder. A similar result can be achieved by controlled oxidation of the lignin precursor powder although this can be more difficult to control than oxidation of the formed monolith. It is also possible, and potentially beneficial, to use both pre and post oxidation.

Accordingly the invention provides a method for producing a carbonisable shaped resin body which comprises:

(a) providing solid particles of a pure water insoluble lignin powder and mixing these with
   (i) particles of a cured meso/macro porous phenolic resin or
   (ii) a milled powder produced from naturally occurring precursors where the precursor has been dried thoroughly and then milled and where the second component can be optionally gently pre-oxidized to assist the milling process;
(b) forming the mixture into a dough; and
(c) extruding the dough to form a shaped product.

The dough may be extruded to form a shaped body having walls defining a multiplicity of internal channels for fluid flow, the channels being directed along the extrusion direction. The extruded structure may be carbonised and may be further activated by treating in flowing carbon dioxide at a temperature of at least 850° C. preferably 900° C. for a time selected to give a required weight loss which may be at least 20% preferably 25%. The resulting carbonised material may be a square channel monolith of 100-1000 μm cell dimension and cell walls with thickness 100-1000 μm. The cell density may be at least 600 channels per square inch e.g. at least 1000 channels per square inch.

The invention further provides a monolith structure which is an elongated body of carbon having walls defining a multiplicity of internal transport channels for fluid flow longitudinally through said body, the carbon comprising particles of microporous and mesoporous and/or macroporous carbon dispersed in a matrix of microporous carbon. The present monolith structure may be the product of the method of any method described herein. It may be provided with a shrink wrap covering its longitudinal exterior surface for preventing in use leakage or escape of blood, serum or plasma. A flow-through chamber may be provided for connection into extracorporeal blood treatment apparatus having a flow path for the extracorporeal blood, an inlet for the flow path at one end of the chamber, an outlet for the flow path at an opposed end of the chamber and arranged within the chamber for through-flow of extracorporeal blood a monolith structure as defined above. The wall of the chamber may be of medical grade plastics material and seal to the ends of the monolith may be by compression members and O-rings or the like. It will be appreciated that a minimum of mechanical strength in the monolith is needed to resist the sealing and other forces encountered in manufacture of the through-flow chamber and in service. The invention further provides extracorporeal blood treatment apparatus including a flow-through chamber as defined above.

A carbonised monolith is provided comprising mesoporous and/or macroporous carbon particles dispersed in a matrix of microporous carbon particles with voids between the particles defining paths for fluid to flow into and through the structure. The monolith may take the form of a shaped body having walls defining a multiplicity of internal transport channels for fluid flow, the transport channels being directed along the extrusion direction. The monolith may be made by carbonising a shaped phenolic body based on phenolic resin precursors. In a method for producing such a carbonisable shaped resin body solid particles of a first phenolic resin are provided which is partially cured so that the particles are sinterable but do not melt on carbonisation. The particles of the first phenolic resin are mixed with particles of a second phenolic resin that has a greater degree of cure than said first phenolic resin and has a mesoporous and/or macroporous microstructure that is preserved on carbonisation. The resulting mixture is formed into a dough e.g. by mixing the resin particles with methyl cellulose, PEO and water, after which the dough is extruded to form a shaped product and stabilizing in its shape by sintering.

The invention further provides carbon having mesopores and micropores/macropores in a bimodal pore distribution and derived by carbonisation of lignin and a novolac resin for use in the extracorporeal treatment of blood for any of:

(a) treating chronic kidney disease;
(b) removal of albumin-bound indoxyl sulphate, p-cresyl sulphate or inflammatory cytokines linked to end stage renal disease;
(c) treatment of liver disease;
(d) removal of phenol, tryptophan, cholic acid or bilirubin;
(e) treatment of sepsis/systemic inflammatory response syndrome;
(f) treatment of alcohol poisoning; and
(g) treatment of cardiovascular disease.

The invention yet further provides a method of extracorporeal treatment of blood which comprises passing the blood in an extracorporeal circuit through a carbon monolith as defined herein for of any of:

(a) treatment of chronic kidney disease;
(b) removal of albumin-bound indoxyl sulphate, p-cresyl sulphate or inflammatory cytokines linked to end stage renal disease;
(c) treatment of liver disease;
(d) removal of phenol, tryptophan, cholic acid or bilirubin;
(e) treatment of sepsis/systemic inflammatory response syndrome;
(f) treatment of alcohol poisoning; and
(g) treatment of cardiovascular disease.

The carbon monolith may for example be derived by extrusion of lignin and mesoporous particles of a cured novolac resin.

The invention is further defined in the accompanying claims to which attention is directed and each of which is incorporated here by reference.

BRIEF DESCRIPTION OF THE DRAWINGS

How the invention may be put into effect will now be described by way of example only with reference to the accompanying drawings in which:

FIG. 1 is a set of three diagrams and one photograph illustrating the structure of a monolith;

FIG. 2 is a photograph showing three carbon monoliths;

FIG. 3 is a table showing the composition of lignocelluloses as a function of the precursor;

FIG. 4A shows formulae for primary lignin components p-coumaryl-, coniferyl- and sinapyl alcohols, dominant building blocks of the amorphous lignin polymer, and FIG. 4B is a model structure for spruce-derived lignin;

FIG. 5 shows the particle size distribution of jet-milled resin of Example 2;

FIG. 6 shows density as a function of pore former and HMTA content for the monoliths of Example 3;

FIG. 7 shows the variation in mercury pore volume with HMTA content for the macroporous (TE7) powder and monoliths of Example 3;

FIG. 8 shows 3 point bend test results for the extruded rods of Example 4 and in particular the impact of cured resin content and degree of cure of the microporous resin content on strength of the carbonised extrudate;

FIG. 9 shows the effect of binder resin cure on the pore structure of the monoliths;

FIG. 10 compares the strength and porosity as a function of binder resin concentration;

FIG. 11 shows the impact of lignin binder content on monolith pore structure and compares this with the pore structure of a resin bound monolith;

FIG. 12 shows a comparison of theoretical pore volume based on lignin dilution with observed pore volume;

FIG. 13 shows the change in crush strength and weight loss on carbonisation as function of the lignin:resin ratio;

FIG. 14 is a photograph of a 100% lignin monolith after pyrolysis;

FIG. 15 shows the nitrogen pore size distribution of bead carbons as a function of the ethylene glycol pore former (E3 to E6) concentration for a pure novolac resin precursor (ethylene glycol modified J1098F novolac resin);

FIG. 16 shows the nitrogen pore size distribution of beads produced from varying resin:organosolv lignin (OSL) ratios and a low ethylene glycol (EG) pore former concentration (E3);

FIG. 17 shows the nitrogen pore size distribution of beads produced from varying resin:organosolv lignin (OSL) ratios and an intermediate ethylene glycol (EG) pore former concentration (E5);

FIG. 18 is a schematic of a monolith cross section showing the definition of the unit cell and three shadow graphs showing the actual cross section of 7 mm, 600 and 1300 CPI monoliths and a 30 mm 600 CPI monolith;

FIG. 19 shows the nitrogen adsorption isotherms for a rage of rice husk-lignin based monoliths;

FIG. 20 is a block diagram showing a whole blood or plasma perfusion system for small monoliths;

FIG. 21 is a graph showing the removal of IL6 from plasma using the lignin bound monolith and the test system in FIG. 20;

FIG. 22 shows removal of IS using lignin bound monoliths. IS remaining in the plasma sample after 5, 30, 60 and 120 minutes of circulation through tested AC monoliths: TE7/Lignin (90-10) (inverted triangles). TE7/Lignin (75-25) (triangles), TE7/Micro (50-50) (circles) and TE7/Lignin (50-50) (squares). A control ( ) was also included as a reference (SEM±n=3);

FIG. 23 shows the PCS (p-cresyl sulphate) remaining in the plasma sample after 5, 30, 60 and 120 minutes of circulation through monoliths: TE7/Lignin (90-10) (inverted triangles), TE7/Lignin (75-25) (triangles), TE7/Micro (50-50) (circles) and TE7/Lignin (50-50) (squares). A control (diamonds) was also included as a reference (SEM±n=3);

FIG. 24 shows the removal of spiked cytokine marker IL-6 from human plasma pool by carbon monoliths. (A) the IL-6 removal expressed as percentage of IL-6 concentration at time 0; (B) the removal of IL-6 is expressed as ng of IL-6 adsorbed by each gram of activated carbon;

FIG. 25 shows the removal of spiked albumin bound uraemic toxin marker PCS from human plasma pool by carbon monoliths. (A) the percentage of PCS removed; (B) the amount of PCS (µmol) adsorbed by each gram of activated carbon;

FIG. 26 shows the removal of spiked albumin bound uraemic toxin marker indoxyl sulphate (IS) from human plasma pool by carbon monoliths. (A) the percentage of IS removed, (B) the amount of IS (µmol) adsorbed by each gram of activated carbon;

FIG. 27 shows the adsorption of IL6 and TNF from plasma in 30 mm diameter lignin bound monoliths;

FIG. 28 shows adsorption of PCS and IS from circulating plasma using 30 mm lignin bound monoliths;

FIG. 29 shows adsorption of PCS, IS, IL6 and TNFα from whole blood using 30 mm monoliths;

FIG. 30 shows adsorption of Staphylococcal enterotoxin B (SEB) from human plasma using carbon beads with 1 nm pores (carbon 1), 30 nm pores (Carbon 5) and 100 nm pores (carbon 9);

FIG. 31 shows the amount of tryptophan removed from the spiked human plasma. Samples were collected after the 0.6 ml of AC beads (A-1, A-2, A-3, A-4 and A-5) incubated with 5.4 ml of tryptophan (0.1 µmol/ml) spiked fresh frozen human plasma for 5, 15, 30 and 60 min, and analysed using HPLC. Tryptophan removal was calculated based on the volume of the AC beads. (Mean n=4, ±SEM);

FIG. 32 shows the adsorption kinetics of bilirubin by AC1-5 from spiked plasma. The adsorption kinetics of bilirubin by 0.4 ml microporous carbon (A1), mesoporous carbon (A2) and macroporous carbon (A3, A4 and A5) from 5.6 ml 300 µM bilirubin spiked plasma was observed at 4 time points over 60 min of incubation period. (Mean n=5, ±SEM); and FIG. 33 shows the reduction in Bilirubin content of circulating blood of a bile duct ligation (BDL) animal model of liver failure during haemoperfusion using a macroporous carbon monolith (upper line) and sham control (lower line).

DETAILED DESCRIPTION OF PREFERRED EMBODIMENTS

Preliminary Discussion

As used herein, the term "microporous" refers to a carbon or other material possessing pores with diameter<2 nm, as measured by nitrogen adsorption and mercury porosimetry methods and as defined by IUPAC.

As used herein, the term "mesoporous" refers to a carbon or other material possessing alongside micropores, pores with diameter from ca. 2 nm to ca. 50 nm, as measured by nitrogen adsorption and mercury porosimetry methods and as defined by IUPAC.

As used herein, the term "macroporous" refers to a carbon or other material possessing alongside micropores and mesopores, pores with diameters larger than 50 nm. This is preferably measured by mercury porosimetry methods and as defined by IUPAC, comprises pores of greater than 50 nm diameter.

By "monolithic" is meant that the resulting porous carbon is in a single piece i.e. not granular or not composed of granular carbons bound together by a binder, for instance a polymer etc. and is composed entirely of carbon. The monolithic carbon may contain large transport channels in addition to inter-particle voids within the walls of the transport channels and the macro/meso/microporosity of the individual particles. For a symmetrical monolith (FIG. 1) a continuous channel structure is defined by a channel dimension, W, and a wall thickness, t, or for an asymmetric monolith by channel length and width or other relevant dimensions as well as wall thickness t. These fix the ratio of open to closed area and therefore the flow velocity along the channels of the monolith. The walls of monolithic carbon have a void structure providing paths for fluid to flow into and through the carbonaceous body of the monolith. Alternatively the product can be formed as a moulded or extruded structure with similar micro and macro pores but lacking the channel structure. FIG. 2 shows the actual structure of three carbonised monoliths of ~7, 20 and 30 mm diameter.

In relation to monoliths, inter-particle voids are spaces formed within a structure that has been created by sintering solid partially cured resin particles and carbonising and activating the resulting sintered material. Such voids may have sizes of the order of about 5 μm but typically is ~20% of the size of the powdered resin used to produce the monolith.

By "sintering" we mean a step which causes the individual particles of phenolic resin to adhere together without the need for a separately introduced binder, while retaining their individual identity to a substantial extent on heating to carbonisation temperatures. Thus the particles must not melt after forming so as to produce a molten mass of resin, as this would eliminate the internal open void structure of the article. Even partial melting can degrade the form of the monolithic structure. The open void structure (as opposed to the closed cells found in certain types of polymer foams) is believed to be important in enabling formed particles to retain their shape on carbonisation.

The lignins are a major component of all plant (lignocellulosic) materials. Plants comprise crystalline cellulose, hemi (amorphous) cellulose and lignin. The proportion of the three components varies with the precursor which range from grasses, plants such as hemp to hard and soft woods. Typical compositions are shown in 3.

Lignin is an amorphous copolymer of phenyl propene units formed via a radical copolymerisation of coumaryl alcohol, coniferyl alcohol and sinapyl alcohol (FIG. 4A). The three dimensional nature of a soft wood (spruce) derived lignin is shown schematically in FIG. 4B.

If the higher plants are considered there are two main types of lignin where these precursor molecules are present in different proportions depending on the organic precursor. Hardwoods comprise a mixture of coniferyl and sinapyl building blocks whilst softwood lignin comprises more than 90% coniferyl alcohol. The resulting lignin is essentially a naturally occurring, medium molecular weight phenolic resin where the thermoplastic behaviour is a function of the composition which in turn depends on the precursor. As such it gives a high carbon yield on pyrolysis which is critical to achieve the good binder performance we have observed. Surprisingly however the binder performance is significantly enhanced when compared with synthetic phenolic resins of similar molecular weight. Whilst not wishing to be bound by the explanation the applicants believe that this is due to different melt flow characteristics of the two materials. As such the performance of the lignin materials in the processes described in this specification will be influenced by the melt flow and therefore by the precursor material.

At present lignin is generally a waste by-product of bio-refining and paper making where cellulose is generally the desired component. In paper making by the Kraft process lignin is generally produced as the acidic black liquor although it is also produced as a relatively pure material by for instance the Organosolv process (U.S. Pat. No. 3,585,104 Kleinert) which is used to extract the lignin in solution which is then precipitated. The lignin from the traditional Kraft process cannot be used in the process of this invention due to the high level of contaminants but more critically its water solubility which precludes the use of a conventional aqueous extrusion processes. The preferred material is produced by processes such as Organosolv and is a high purity water-insoluble powder that can be used in extrusion and other forming processes. In particular its metal content is low, preferably only a few ppm.

According to the Kleinert patent the Organosolv process involves digesting subdivided fibrous plant material in a digester at an elevated digesting pressure and at an elevated digesting temperature without pre-impregnation of pulping agent. Kleinert explains that aqueous mixtures of the lower aliphatic alcohols, such as methanol, ethanol, propanol, and aqueous mixtures of the lower aliphatic ketones, such as acetone, or aqueous mixtures containing both lower aliphatic alcohols and lower aliphatic ketones are appropriate pulping agents, aqueous mixtures of ethanol in the range 20%-75 wt % ethanol being preferred. The claimed process comprises:

(a) feeding said subdivided fibrous plant material to an inlet of said digester and moving said fibrous plant material through the digester to a fibrous plant material outlet remote from said inlet;

(b) introducing a liquid pulping agent into said digester at a point intermediate the fibrous plant material inlet and the fibrous plant material outlet, said pulping agent being at a temperature corresponding essentially to said digesting temperature, and being an aqueous mixture of a member selected from the group consisting of a lower aliphatic alcohol, a lower aliphatic ketone and their mixtures and containing about 20-75 wt %1 of said member;

(c) flowing said pulping agent in counter current contact with said fibrous plant material, heating said fibrous plant material to substantially said elevated digesting temperature substantially immediately on its being fed into said digester, and dissolving non-cellulosic water-soluble components of said fibrous plant material in said pulping agent on its being contacted with said pulping agent;

(d) withdrawing pulping agent containing said non-cellulosic components from said digester at a point adjacent said subdivided fibrous plant material inlet, said withdrawn pulping agent having a temperature corresponding substantially to said elevated digesting temperature so that no appreciable cooling of the withdrawn pulping agent occurs; and (e) withdrawing digested fibrous plant material from said digester through said fibrous plant material outlet.

An advantage for this invention is that the cost of the lignin, essentially a waste material, is lower than synthetic oil derived phenolic resins. It can also be available in very large quantities. A further advantage of lignin in this invention is that as it is essentially a naturally occurring phenolic resin the carbon yield during pyrolysis is high, typically around 30%. This is lower than that achieved with the synthetic phenolic resin, primarily reflecting loss of the side chains, but is none the less significantly higher than the <20% yield typically achieved with cellulosic precursors. The applicants believe that all water insoluble lignins will be usable in the processes of the current invention but that some benefits may be achievable through the use of different lignins with selected melt flow characteristics depending on the proposed end use, whether as binder, structure modifier or the main structure forming component.

In some embodiments the invention is concerned with the production of complex structures that can be extruded or moulded and comprise a range of precursor particles combined with lignin either as the binder (first phase) or as the main structural component. The lignin can be used in combination with porous resin structures produced by methods such as those disclosed in U.S. Pat. No. 8,383,703. In this case the similar carbon yield and volume shrinkage of the lignin binder and resin matrix components gives good strength at a low binder level, maximising the mesoporosity in the finished carbon. However the lignin can also be used in conjunction with a wide range of inorganic materials, such as zeolites and silicas, and other activated carbon powders but is limited to precursors with sufficient thermal stability to withstand the firing process. However in the case of the inorganic materials, which do not shrink during the firing process, the strength is reduced.

It is also possible to make activated carbon materials from the lignin as the main, second phase either by the inclusion of phenolic resins in the starting mixture, which inhibit the melt flow characteristics of the lignin, or by oxidation stabilisation of the lignin whereby it is possible to produce structured materials from 100% lignin. We have found that the microstructure of the carbon derived from the lignin bears a striking similarity to the unique pore structure exhibited by synthetic phenolic resin derived materials.

Applications of Lignin Modified Materials

The various ways in which the lignin can be utilised and the products so formed can be utilised are summarised below:—

1. Lignin as binder (first) phase. In this instance the product properties are controlled mainly by the second phase.
(a) If the second phase is the fully cured meso/macro porous resin the binder concentration should be adjusted to give the maximum strength and attrition resistance consistent with maintaining the maximum concentration, and therefore pore structure properties, of the second phase.
(b) The second phase may also be a naturally occurring material prepared from e.g rice husk, flax waste or any other naturally occurring precursor. In this instance the allowed binder content be higher, consistent with the production of mechanically stable product, as the goal is to make a low cost monolithic structure. Here the pore structure derives primarily from the second phase which tends to be more reactive. Some porosity does however derive essentially from carbonisation of the lignin component
(c) In (a) and (b) the second phase is pyrolysable. It is also possible to use a non pyrolysable second phase such as activated carbon or a porous inorganic material such as a zeolite. In this instance the lack of shrinkage in the second phase still leads to mismatched shrinkage. This will give inferior mechanical properties which could necessitate the use of higher lignin binder levels
2. Lignin as the second phase. In this instance the properties of the final carbon material will derive primarily from the structure created by the lignin. Here the problem is preventing the lignin from melting and foaming
(a) We have surprisingly found that the melt flow/foaming characteristic of the lignin can be inhibited by adding cured novolac resin to the mixture. In this instance whilst 100% of the lignin foams and cannot be used, in the presence of 10% cured novolac powder it is possible to produce strong extruded materials although the stability is improved with 20% lignin.
(b) Alternatively the melt flow characteristics can be totally inhibited by either pre-oxidising the lignin powder and then extruding this normally or by forming the monolithic structure from as received lignin powder and then post oxidizing the extruded structure prior to carbonisation. In both cases the product carbon comprises 100% of the lignin precursor.
3. Production of meso/macro porous materials by solution dispersion. This is an extension of the standard method for producing the meso/macro porous beads disclosed in WO 02/12380 where a solution of the novolac resin and curing agent in ethylene glycol is dispersed into hot oil. Alternatively the resin solution/curing agent can be poured into a tray, cured and then ground to a powder of the required size. In this instance the resin solution comprises a mixture of the standard novolac resin, the lignin and the HMTA curing agent which is then processed by dispersion into hot oil or by block curing and milling. These processes can produce finished resins with significantly higher porosities than can be achieved with a resin glycol solution with the same level of glycol pore former. The porosity is controlled by the novolac:lignin ratio and the total resin:glycol ratio.
4. Medical applications for monoliths;

The active carbon component in the monolithic structures has the same micro:meso/macro binary pore structure that has been shown to be the critical component in the bead carbons used in extra-corporeal blood processing (ref) and the examples later in this document demonstrate similar adsorption properties for the small, middle and larger molecule weight molecules. However, given the hydrodynamic properties of the monoliths this performance is surprising in its own right but has now been shown to be critically dependent upon the channel size (W) and structure of the monoliths (see FIG. 1). In particular, it has been shown that the cell density should exceed 600 cells per square inch (cpi) and preferably exceed 1000 cpi.

More surprisingly we have now shown that haemolysis in the blood stream flowing through the monolith is significantly reduced when compared to the packed beds of beads used in the earlier work (ref). In the absence of heparin, which is required in all dialysis procedures to prevent thrombosis, the time to the point where clotting is observed increase from 10-12 minutes in packed bead column to 20-25 minutes in the monoliths. Whilst heparin cannot be eliminated from the procedures it has been shown that the level required can be dramatically reduced and this then substantially reduces the risk of internal bleeding which is a significant problem.

(a) The experimental data evidenced in this patent is in support of the application of the monoliths as a blood purification treatment for chronic kidney disease (CKD). The monolith in this instance would be used to augment current renal replacement therapies such as haemodialysis, to remove uraemic toxins that are currently poorly removed. These applications are critically dependent upon the bimodal—micro plus meso/macro porous structure of the monoliths to achieve the removal of molecules with molecular weights ranging from 100's to 56000, whilst having mechanical properties that prevent the shedding of carbon particles into the blood stream.

Mesoporous monoliths of this invention are able to remove a range of uraemic toxins from plasma and blood including, the albumin bound toxins indoxyl sulphate and p-cresyl sulphate which remain in the blood after haemodialysis and have been linked to progression of CKD, the high morbidity and mortality rates for end stage renal disease (ESRD) and cardiovascular disease (CVD). The monoliths are also able to remove larger sized biotoxins such as the inflammatory cytokines and other contrary substances linked to ESRD.

Other potential haemoadsorption applications for the mesoporous monoliths revolve around the removal of endogenous or introduced toxins from patient's blood. These include:—
(b) Liver Disease Acute-on-chronic liver disease (ACLF) is characterised by a rapid loss of function in up to 90% of a patient's liver cells. Extracorporeal liver support devices could detoxify the blood of ACLF patients and act as a bridge to transplantation. The carbon monoliths are designed to adsorb small and medium-sized hydrophobic molecules (e.g. cytokines) that cannot be removed by conventional water-based dialysis.

The controlled pore structure carbons are also effective at removing the albumin bound liver toxins which include tryptophan, cholic acid and bilirubin. To date these tests have only been carried out using the bead form carbons which demonstrate clearly the critical role of pore structure.

Without wishing to be bound by this explanation we believe that the removal of these toxins does not take place via the adsorption of the albumin bound complex but rather that the equilibrium below is displaced towards the carbon-toxin as a function of the relative strength of adsorption of the toxin in the carbon and the albumin binding constant.

Carbon-toxin⇌albumin-toxin

For this to occur the carbon must contain both the larger pores necessary for the complex to initially become associated with the carbon and then for the smaller pores to adsorb the toxin. This toxin adsorption is then related to the size and shape of the toxin and the structure of the micropores.

Although the majority of the tests have to date been carried out with the beads we believe that the similarity of the pore structure in the bead and monolith carbons and the performance of the monoliths in the other separations shown herein clearly indicate that these separations will occur over the monolithic carbons. The properties of the challenge molecules are summarised in Table 1.

TABLE 1

Properties of Liver Toxins

| Compounds | MWt (g/mol) | $K_A$ (M$^{-1}$) |
|---|---|---|
| Phenol | 94.11 | $1.0 \times 10^3$ |
| Tryptophan | 204.23 | $1.0 \times 10^4$ |
| Cholic acid | 408.57 | $0.33 \times 10^4$ |
| Bilirubin | 584.66 | $9.5 \times 10^7$ |

This is discussed in more detail in example 12.

(c) Sepsis/Systemic Inflammatory Response Syndrome (SIRS)

Another potential haemoadsorption application for the mesoporous monolith is in the treatment of sepsis or systemic inflammatory response syndrome (SIRS). Sepsis is initiated by the presence of bacterial endotoxin or exotoxins, via a series of events the bacterial toxins stimulate the systemic release of a number of pro-inflammatory mediators including cytokines and complement activation products. When released these inflammatory species evoke a systemic inflammatory response. To counteract the process of sepsis it is necessary to reduce the systemic level of both endotoxin/exotoxin and the circulating cytokines that mediate the inflammatory process. The carbon beads have been shown to be successful in removing a range of inflammatory cytokines including TNF, IL-6 and IL-8 as well as both bacterial endotoxin and exotoxins from blood. This work has shown that the monoliths can also remove TNFα, the most difficult of the SIRS related molecules to remove, from both blood and plasma (d) Alcohol Poisoning Alcohol poisoning is a significant problem, particularly in the countries of the former Soviet Union. We have now shown in both in-vitro and in-vivo studies that the monolithic carbons of the current invention can remove alcohol from a flowing blood stream. This is particularly surprising as conventional activated carbons do not typically show any significant affinity for alcohol in adsorption from aqueous streams whereas in these studies high levels of removal have been shown even at the low concentrations in the blood encountered in alcohol poisoning. These test details are discussed in Example 9.

(e) Cardiovascular Complications

Patients undergoing open-heart surgery often exhibit a potentially life threatening inflammatory reaction which is initiated by the presence of pro-inflammatory cytokines present in the blood returning from the cardiopulmonary bypass (CPB) machine. The carbon beads are able to remove a range of inflammatory mediators and as evidenced by the examples relating to cytokine removal and this ability could be transferred to the monolith as a haemoadsorption therapy to treat such cardiovascular complications. The results presented here demonstrate clearly that earlier work that demonstrated removal of these molecules by bead carbon can be replicated in the monolithic structures of the current invention.

Preparation of Structured Nanoporous Materials Using Lignin Binders

We have found that lignin can be beneficially be used as a binder (second component) for a wide range of first components comprising preferably polymer materials that can be co-pyrolysed with the lignin. When both the lignin and the first components shrink to a similar extent during the pyrolysis process the strength of the final product is maximised. In order of preference then the first component comprises:—

(1) Polymeric materials that provide a good yield of nanoporous carbon, for instance but not limited to phenolic resin. In this instance the shrinkage of the first and second component is similar and the strength in the final carbon is maximised.

(2) Lignocellulosic materials and derivatives such as wastes from the processing of hemp, rice, wood etc. that produce carbon on pyrolysis but where the weight yield of the second component is lower, the shrinkage is therefore higher and the strength of the final material is therefore reduced.

(3) Nanoporous materials such as activated carbons. In this case the second component does not shrink on thermal processing. However the nanopore structure of these materials is already formed and the temperature required to stabilise the lignin binder can be reduced substantially, limited only by final use considerations.

Irrespective of the first component the method of production of the structured composite material is the same. This can be by either extrusion or pressurised moulding. In the case of extrusion the first component, preferably with a particle size between 20 and 100 μm is mixed with between 10 and 40% volume of the lignin binder powder (second component) along with the extrusion aids. The extrusion aids are well known to those skilled in the art but comprise primarily cellulose compounds such as Methocell, polyethylene oxide and other additives used to modify and control the rheology of the dough and water. The amount of water to be added depends on the porosity of the first component but should be sufficient to give a flexible dough.

Embodiments of present materials incorporate a wide range of pore structures depending on the nature of the first component. Where the first component is the resin powder produced by solvent pore forming, the final material contains both micropores and relatively large mesopores ((20-50 nm) and optionally macropores (>50 nm). Typically, a precursor resin formulation is used which comprises a proportion of pore former off for instance 250 parts ethylene glycol to 100 parts of resin-forming components. This provides macropores that are useful e.g. for adsorption of peptides and proteins e.g. cytokines in blood. Larger macropores in carbonised and optionally activated material of size e.g. 200-2000 nm arise from voids between the sintered particles of resin precursor and provide pathways for gas or liquid to permeate into the structure, but do not adsorb protein.

In the case of natural precursors such as rice husks or hemp shives the final pore structure reflects the structure that would be derived by pyrolysis of these materials alone combined with the micropore structure that derives from the lignin binder.

Preparation of Structured Porous Carbon from Meso/Macro Porous Phenolic Resin as the Second Component The applicants have developed a number of processes for the production of activated carbon from phenolic resin with a microporous or mesoporous/microporous structure, the products commonly taking the form of beads, and the underlying process for producing the meso/macro porous resin is applicable in the present invention.

Nanoporous Phenolic Resins—Nucleophilic Component

Resins for making carbonaceous material can be prepared from any of the starting materials disclosed in WO 02/12380. Nucleophilic components may comprise phenol, bisphenol A, alkyl phenols e.g. cresol, diphenols e.g. resorcinol and hydroquinone and aminophenols e.g. m-aminophenol.

It is preferred to use as nucleophilic component a phenolic novolac or other similar oligomeric starting material which, because it is already partly polymerized, makes the polymerization to the desired resin a less exothermic and hence more controllable reaction. The preferred novolacs have average molecular weights (AMW) in the range of from 300 to 3000 prior to cross-linking, corresponding to a degree of polymerisation (DP) with respect to phenol of about 3-30 and may be solids with melting points in the region of 100° C. Novolac resins of AMW less than 2000 and preferably less than 1500 form resins which on carbonisation tend to produce carbons with desired pore size distributions using lower amounts of pore former. Novolacs are thermally stable in that they can be heated so that they become molten and cooled so that they solidify repeatedly without structural change. They are cured on addition of cross-linking agents and heating. Fully cured resins are infusible and insoluble.

Whilst commercial novolacs are largely produced using phenol and formaldehyde, a variety of modifying reagents can be used at the pre-polymer formation stage to introduce a range of different oxygen and nitrogen functionalities and cross-linking sites. These include but are not limited to:—

(a) Diphenols e.g. resorcinol and quinines e.g. hydroquinone. Both are more reactive than phenol and can lead to some cross-linking at the pre-polymer production stage. It is also possible to introduce these compounds at the cross-linking stage to provide different cross-linking paths. These also increase the oxygen functionality of the resins.

(b) Nitrogen containing compounds that are active in polycondensation reactions, such as urea, aromatic (aniline, m-amino phenol) and heteroaromatic (melamine) amines. These allow the introduction of specific types of nitrogen functionality into the initial polymer and final carbon and influence the development of the mesoporous structure of both the resins and the final carbons. Like hydroquinone and resorcinol, all the nitrogen containing nucleophilic modifying reagents which can be used possess two or more active sites and are more reactive in condensation reactions than phenol or novolacs. It means that they are first to react with primary cross-linking agents forming secondary cross-linking agents in situ.

The nucleophilic component may be provided alone or in association with a polymerization catalyst which may be a weak organic acid miscible with the novolac and/or soluble in the pore former e.g. salicylic acid, oxalic acid, phthalic acid or p-toluene sulfonic acid (but preferably not for resins intended to be carbonied as the addition of sulphur-containing compounds is undesirable).

The concentration of novolac in the pore former may be such that when combined with the solution of cross-linking agent in the same pore former the overall weight ratio of pore former to (novolac+crosslinking agent) is at least 125:100 by weight. The actual ratios of novolac:pore former and crosslinking agent:pore former are set according to convenience in operation e.g. in the case of the process disclosed in WO 2008/043983 (Tennison) by the operational requirements of a bead production plant and are controlled by the viscosity of the novolac:pore former solution such that it remains pumpable and by the ratio of crosslinking agent:pore former such that the crosslinking agent remains in solution throughout the plant.

Cross-Linking Agents for Phenolic Resins

The cross-linking agent is normally used in an amount of from 5 to 40 parts by weight (pbw) per 100 parts by weight of the nucleophilic components e.g. novolac, typically from 10 to 30 (e.g. 10, 15 or 20) pbw cross-linking agent per 100 pbw of nucleophilic component. It may be, for example, an aldehyde e.g. formaldehyde or furfural or a polyamine e.g. HMTA, melamine or hydroxymethylated melamine. HMTA is preferably used as cross-linking agent.

For a partially cured and sinterable resin material there may be employed up to 5 pbw of HMTA per 100 pbw of novolac. However for the production of the mesoporous/macroporous resin it is essential that the resin is fully cured. HMTA or other cross-linking agents are preferably used at a proportion of 15 to 25 pbw. Whilst the stoichiometric amount required for complete curing is approximately 15%, a level of 20% is preferably used to guarantee full curing. This ensures formation of the solid resin with maximal cross-linking degree and ensures the stability of the mesopore structure during subsequent removal of the pore former. At lower degrees of cross linking the structure tends to collapse during removal of the pore former prior to pyrolysis.

Pore-Formers

The pore former also acts as solvent. Thus, the pore former is preferably used in sufficient quantities to dissolve the components of the resin system, the weight ratio of pore former to the total components of the resin system resin being preferably at least 1.25:1.

Details of suitable pore formers are given in WO 02/12380 (Tennison). The pore former may be, for example, a diol, a diol-ether, a cyclic ester, a substituted cyclic or linear amide or an amino alcohol e.g. ethylene glycol, 1,4-butylene glycol, diethylene glycol, triethylene glycol, γ-butyrolactone, propylene carbonate, dimethylformamide, N-methyl-2-pyrrolidinone and mono ethanolamine, ethylene glycol being preferred, and where the selection is also limited by the thermal properties of the solvent as it should not boil or have an excessive vapour pressure at the temperatures used in the curing process.

It is thought that the mechanism of mesopore and macropore generation within the individual particles of polymer is due to a phase separation process that occurs during the cross-linking reaction. In the absence of a pore former, as the linear chains of pre-polymer undergo cross-linking, their molecular weight initially increases. Residual low molecular weight components become insoluble in the higher molecular weight regions causing a phase separation into cross-linked high molecular weight domains within the lower molecular weight continuous phase. Further condensation of light components to the outside of the growing domains occurs until the cross-linked phase becomes essentially continuous with residual lighter pre-polymer trapped between the domains. In the presence of a low level of pore former the pore former is compatible with, and remains within, the cross-linked resin domains, (e.g., <120 parts/100 parts Novolac for the Novolac-HMTA-Ethylene Glycol reaction system), whilst the remainder forms a solution with the partially cross-linked polymer between the domains. In the presence of higher levels of pore former, which exceed the capacity of the cross-linked resin, the pore former adds to the light polymer fraction increasing the volume of material in the voids between the domains that gives rise to the mesoporosity and optionally macroporosity. In general, the higher the pore former content, the larger the wider the mesopores up to macropores and the higher the pore volume.

This phase separation mechanism provides a variety of ways of controlling the pore development in the cross-linked resin structures. These include chemical composition and concentration of the pore former; chemical composition and quantity of the cross-linking electrophilic agents, presence, chemical nature and concentration of modifying nucleophilic agents, chemical composition of phenolic nucleophilic components (phenol, novolac), presence, chemical nature (acidic, basic), the presence of water within the solvent and concentration of any curing catalyst if present.

Both protic and aprotic solvents of different classes of organic compounds match these requirements and can be used as pore formers, both individually and in mixtures. In addition to dissolving the reactive components and any catalyst, the pore former should also, in the case of phenolic resins, be compatible with water and/or other minor condensation products (e.g. ammonia) which are formed by elimination as polymerization proceeds, and the pore former is preferably highly miscible with water so that it can be readily removed from the polymerized resin by washing.

Production of Resin Precursor

For the purposes of monoliths or other structures WO 02/12380, discloses the production of the resin in powder rather than bead form. For the production of shaped structures, such as monoliths, a resin powder is required with a mean particle size of 20 to 100 µm, preferably around 40 µm. This is manufactured by producing a mixed solution of the resin component and the cross linking agent in the pore forming solvent. This typically comprises a medium molecular weight novolac, although the molecular weight is not critical, and HMTA dissolved in the pore forming solvent, preferably ethylene glycol (EG). The two solutions, HEX:EG and Novolac:EG are produced separately as they can be heated to enhance the dissolution. A critical requirement for the pore forming solvent is that it dissolves both the resin and crosslinking agent. The two cold solutions are then mixed. The novolac:hex composition is 100 parts:20 parts whilst the ratio of EG:HEX+novolac is increased to increase the meso/macro pore volume. The mixed solution is then cured which requires a temperature of approximately 150 C. This can either be in batch mode, where the mixture is poured into trays and then placed into a preheated oven, and which gives rise to blocks of cured resin which then require granulation, or in a continuous rotary oven where the product may be large granules. The glycol can be removed by washing or vacuum drying and the particle size of the cured resin for washing is preferably a 1-2 mm which can be produced by granulation.

Production of Carbon in Monolithic Form

Standard monoliths of carbon produced from phenolic resins by existing processes have a microporous/inter-particle macroporous void structure and introduction of mesoporosity or macroporosity in the individual particles of resin precursor and then of carbon was not initially intended. Forming monoliths having mesoporosity or macroporosity intentionally introduced into the structure of the individual particles from which the monolith is formed gives rise to a number of difficulties. Normally to produce the microporous monoliths it is necessary that the partially cured resin should be in a sinterable state, and that requirement limits the amount of cross-linking agent that can be used. The standard process used by the applicants for making monolithic carbon from phenolic resins uses 5 parts by weight of HMTA as cross-linking agent, but if the same amount is used in the production sequence indicated for the production of meso/macro porous resins the resin remains in a liquid state and even at 10 parts HMTA the resin is barely solidified, and the mesoporosity or macroporosity induced in the individual particles collapses during pore former removal. It is therefore desirable to increase the proportion of cross-linking agent to an amount sufficient to stabilise the meso/macroporous structure.

We have shown that the meso/macro porous structure of the individual particles can only be stabilised by complete cure, typically using at least 15 parts of HMTA and preferably 20 parts curing agent per 100 parts resin. This material cannot be adequately sintered and it is therefore essential to use a separate binder component. For the production of monolithic structures the lignin, typically at between 10 and 30% weight loading is mixed with the meso/macro porous resin power described above. The extrusion aids comprising materials well known to those skilled in the art, but comprising primarily methyl cellulose and polyethylene oxide, are mixed with the precursor powder and lignin powder. Water is then added to produce a pliable dough. The resulting dough can then be moulded or extruded and then dried. At this stage the resulting green body is fired to a minimum of 500° C., preferably greater than 700° C. which is required to decompose the extrusion aids which at lower temperatures tend to block the pore structure.

The cell geometries that have been produced are limited at the high cell density end of the spectrum by the pressure drop through the monolith when in use, especially when using complex, high viscosity fluids such as blood but also the by the ability to produce the fine channel and hole structure in the extrusion die and the pressures required to actually extrude the dough. The geometry at the low cell density end of the spectrum is limited by the performance of the carbon monolith in the separation process. We have shown that the separation performance drops rapidly at below approximately 600 cpi.

The structures of the monoliths produced and tested in this application are summarised below for the three typical monoliths that have been used with nominal carbon diameters of 7, 20 and 32 mm. A key factor here is the monoliths shrink by approximately 30% radially and axially. This results in a significant increase in cell density between the extruded resin monolith as can be seen for the 7.9 mm monolith where the cell density in the resin is 645 but in the carbon is 1315.

Whilst monoliths with higher cell density can be produced we believe that this cell geometry represents a reasonable maximum cell density and balance between manufacturability and pressure drop. Nonetheless high densities could probably be produced if required.

| Nominal carbonised | Calculated Extruded resin monolith properties from die structure | | | | Calculated Carbonised monolith properties based on 30% shrinkage | | | | |
|---|---|---|---|---|---|---|---|---|---|
| monolith diameter mm | calculated CPI | diameter | wall thickness | channel size | Calculated CPI | diameter | wall thickness | channel size | Unit cell |
| 7.9 | 286 | 10.5 | 600 | 900 | 585 | 7.9 | 450 | 675 | 1125 |
|  | 645 | 10.5 | 400 | 600 | 1316 | 7.9 | 300 | 450 | 750 |
| 20 | 329 | 27 | 500 | 900 | 671 | 20.3 | 375 | 675 | 1050 |
| 32 | 287 | 420 | 500 | 1000 | 585 | 31.5 | 375 | 750 | 1125 |
| 32 | 413 | 420 | 500 | 750 | 840 | 320 | 375 | 562 | 937 |

Carbonisation and Activation

The transformation of the lignin bound structures into nanoporous structures is performed by carbonisation, i.e. high temperature treatment in an inert atmosphere and at temperatures from ~500° C. upwards and where necessary activation. The pyrolysis process begins at about 400° C. and is largely complete by around 700° C. although further small weight losses continue up to around 1400° C. However surface area development in the polymeric components is only significant above around 700° C. at which point the material is not strictly carbon but a pyropolymer. The inert atmosphere for pyrolysis can be secured by flowing suitable inert gas. Nitrogen and argon can be used as inert purge gases at any temperature whilst carbon dioxide is effectively inert up to around 800° C. in the absence of catalytic metals. Vacuum may also be used. Due to the presence of mesopores in these materials, which provide efficient escape routes for the volatile products, the heating rates employed can be very high—up to 10° C. per minute. The porosity of the carbon component can be further enhanced by conventional activation methods, e.g. by activation in carbon dioxide above 800° C., which can give surface areas as measured by BET 5 point method of up to 2000 m$^2$/g or even up to 3000 m$^2$/g. It has been found that "physical" activation with carbon dioxide at the temperatures in the range 850-900° C. gives rise predominantly to microporosity Examination of the pyrolysed composite resin structures using scanning electron microscopy clearly shows the domains of the lignin derived binder and the second mesoporous resin phase. This confirms that the melt flow characteristics of the lignin are such that the lignin does not flow into the voids either between the particles or to the pores within the resin particles.

The walls of the resulting monolithic carbon have a structure with voids between the particles, the individual continuous void space leading into and through the monolith. The void structure in the walls of a monolith is controlled by the particles used to form the monolith. When the monolith is made from macro-particles with a mean particle size of $D_P$ (FIG. 5) the macro pore size is typically 20% of the size of the precursor mean particle size. The sizes of the individual particles can be varied over a wide range from a maximum particle size of approximately 10% of the wall thickness, t, to a minimum practical particle size of about 10 μm. This gives a void size within the wall for a 1 mm wall thickness of 2-20 μm. The void size fixes the bulk diffusivity of the adsorbent molecules within the matrix. In embodiments the monoliths are square channel monoliths with a cell structure (cells per square cm) where the channel size is between 100 and 2000 μm and the wall thickness is between 10) and 2000 μm and with an open area of between 30 and 60% to give a good carbon packing density per unit volume and acceptable mass transfer characteristics.

How the invention may be put into effect will now be further described in the following example.

Example 1 (Reference)

Preparation of Phenolic Resin in Sinterable Powder Form 4 kg of a mixture of a standard medium molecular weight Novolac (Code J1098, supplied by Hexion Chemicals) in flake form was mixed with 200 g of HMTA. The mixture was jet milled to give a mean particle size of 40 μm. The powder was then placed in a tray and cured using a temperature ramp 3° C./min up to 100° C., dwell at 100° C. for 1 hour, then 3° C./min up to 150° C., dwell at 150° C. for 2 hours and then cooled back to room temperature. The cured block of resin was then hammer milled and jet milled to give a powder with a mean particle size of 40 μm.

Example 2 (Reference)

Preparation of Fully Cured Mesoporous Resin Powder

TE7/20 resin block was prepared as follows. 2841 g of ethylene glycol was mixed with 4315 g of 66.7% novolac resin in ethylene glycol after which HMTA (570 g) in 4276 g ethylene glycol was added to the mixture and stirred. The liquid mixture was then transferred to two metal trays. These were placed in the oven and ramped to 150° C. at 3° C./min at which temperature they were held for 2 hours. During curing ammonia was released which was trapped in a water scrubber. After curing the block of resin was granulated to give approximately 2 mm pieces which were suitable for water washing to remove the glycol. After washing and drying the resin granules were jet milled using a Hosokawa 100AFG mill to give a powder with mean a particle size of 40 μm. The particle size distribution is shown in FIG. 5.

Example 3 (Reference)

Preparation of Mesoporous Monoliths by Control of the Degree of Cure of the Mesoporous Resin The impact of the degree of cure (controlled by the HMTA content) and level of meso/macro porosity in the resin (controlled by the ethylene glycol content) was examined. A matrix of compositions was prepared by producing a mixed solution of the novolac resin and HMTA in the glycol solvent. This was placed in trays and cured at 150° C. for 2 hours, after which it was crushed, water washed to remove the glycol and then milled to a fine powder (<100 μm) (FIG. 5). This was then mixed with water and cellulose ether (Methocell) and extruded into 3 mm rods. After drying at room temperature the rods were carbonised at 80° C. in flowing carbon dioxide. The density of the carbonised monoliths is shown in FIG. 6. The higher density at low HMTA content reflects the loss of internal porosity in the resin particles due to the reduced degree of cure of the mesoporous resin. This is also reflected in the mercury porosimetry data. FIG. 7 shows the porosity after carbonising the extruded rods and after carbonising the precursor powder. Comparing the two results shows that forming the powder into the monolith has had no effect on the size of the pores and little effect on the mean pore size. This shows that subsequent porosity loss was not due to the pressure involved in the extrusion process. It is clear however that at the lower HMTA level there has been a significant loss in porosity for both the powder and the monolith. These results indicate that producing a mesoporous resin with a high sintering potential by under curing is not a viable process due to the collapse of the structure during pyrolysis.

Example 4 (Reference)

Preparation of Rods Using Novolac Resin, Either Uncured or with Low Levels of Cure as Binder Rods were produced using the fully cured mesoporous resin as the main component of the matrix and non-porous phenolic resin with varying degrees of cure as the binder matrix. The binder phase comprised a standard novolac resin cured using either 3 parts or 5 parts weight HTMA (or used in its uncured state. The partially cured resins were prepared by co-milling either 3 or 5 parts of HTMA and novolac (J1098) powder. The mixed powder was then cured in small quantities at 150° C. for 2 hours after which it was re-milled to <100 μm. The rods were formed by nixing these milled resin powders with the milled mesoporous resin powder, forming this into a dough using water and Methocell and extruding this into 3 mm rods. The rods were dried at room temperature and were then carbonised at 800° C. in flowing carbon dioxide.

The 3-point bend test results are shown in FIG. 8 and show the impact of cured resin content and degree of cure of the microporous resin binder on strength of the carbonised extrudate. It is apparent that the strength increases significantly with the binder resin content at levels higher than ~35% wt. It can also be seen that for the uncured resin which melt flows prior to carbonisation there is little improvement in strength until binder levels greater than 55%. This believed to be due to the loss of the binder into mesopores of the fully cured resin component.

This is also reflected in the change in mesoporosity of the carbon products. FIG. 9A shows the impact of the using the 5 pt HMTA cured resin as the binder whilst FIG. 9B shows the impact of using the uncured novolac resin as the binder. It can be seen that at 50% binder addition, there has been a ~40% loss in porosity using the cured resin binder but an 80% porosity loss with the uncured novolac binder. It can be seen that for the 5% HTMA (HMTA5) structures the loss in porosity is greater than would be expected from dilution alone. If there was no effect of adding 50% wt of the resin binder the pore volume should have reduced 1 to 0.5 cm$^3$/g whereas it was reduced to 0.35 cm$^3$/g. For the uncured novolac (0% HMTA) binder the loss was even greater to 0.2 cm$^3$/g suggesting significant melt flow and pore filling of the porous resin component.

The pore volume and strength are compared in FIG. 10 and it can be seen that there is an optimum at around 40% of the binder resin. However the residual pore volume at this formulation makes the product carbon unsuitable for use in applications such as blood filtration.

Example 5A

Preparation of Resin Monoliths Using Lignin as Binder (According to the Invention)

There are two main reasons for producing resin-lignin monoliths. In the first instance it is to provide a route to strong, attrition resistant, meso-macro porous monoliths free from the limitations demonstrated in Example 4. In the second case it is to produce lower cost monolithic structures primarily from the lignin precursor with the minimum content of commercial novolac resin.

a) Meso-Macro Porous Monoliths

Four different monoliths were prepared with the composition listed in Table 1. In addition, polyethylene oxide and Methocell were added were added to each mixture to improve the mixture viscoelasticity to aid the extrusion process. These are compared with the monolith produced in Example 4 where the binder phase was the sinterable partially cured resin (Adept 023) (Table 1)

TABLE 1

Formulation of Various Extruded Monoliths

| Code | Monolith | Microporous Resin (g) | TE7/20 (g) | Lignin (g) | Water (g) | Glycerol (g) |
| --- | --- | --- | --- | --- | --- | --- |
| ADEPT 023 | TE7/Micro 50/50 | 15 | 15 | 0 | 36 | 4.2 |
| ADEPT 024 | TE7/Lignin 50/50 | 0 | 15 | 15 | 30 | 0 |
| ADEPT 025 | TE7/Lignin 75/25 | 0 | 22.5 | 7.5 | 49.6 | 0 |
| ADEPT 026 | TE7/Lignin 90/10 | 0 | 27 | 3 | 56.4 | 0 |
| ADEPT 027 | TE7/Lignin 75/25 | 0 | 22.5 | 7.5 | 49.6 | 0 |

The monoliths were extruded using a 7.5 mm die with 600 cells per square inch (cpi). The extruded TE7/Micro (50/50) monoliths showed a yellow colour, many areas of the monoliths had cracks on the outer surface indicating that the dough was not optimal for extrusion processes. With addition of lignin in the monolith composition the monoliths were dark brown and with increased lignin content, the brown colour intensified. Most importantly, with increase of lignin content, cracks on the monolith outer surface disappeared, and the resulting dried monoliths had smooth outer surface.

TABLE 2

Processing of lignin bound mesoporous resin

| Formulation | | Wt loss | |
|---|---|---|---|
| Lignin | Resin | carbonisation | Activation |
| 10 | 90 | 54.5 | 28.2 |
| 25 | 75 | 55.6 | 29.1 |
| 50 | 50 | 54.7 | 29.3 |
| TE7 20/micro | | 60.7 | 21.7 |

After extrusion the monoliths were carbonised in flowing carbon dioxide with a ramp rate of 5° C./minute to 750° C. After holding at 800° C. for 30 minutes they were cooled back to ambient. They were then activated in flowing carbon dioxide at 900° C. for 2 hours. The weight losses on carbonisation and activation are summarised in FIG. 9. There is no significant difference at lignin levels from 10 to 50 parts weight showing the similarity in the processing of the phenolic resin and lignin components. The sample bound with the sinterable resin shows a lower activation reactivity but had very poor mechanical properties.

The mercury pore size distributions for the materials are shown in FIG. 11. These plots have been truncated at 1000 nm as the intrusion volume above this size is related to the inter-particle voids rather than the internal porosity of the spheres. The internal pores have a size of 55 nm irrespective of the lignin loadings.

FIG. 12 shows the pore volume in the 10-1000 nm pore size range. The diamond-pattern points are the measured pore volumes whilst the square pattern points are the expected pore volume based simply on dilution of the mesoporous resin with the microporous lignin derived material. This demonstrates that the lignin does block some of the desired mesopores although the loss is acceptable at less than 25% lignin.

FIG. 13 shows the crush strength of the lignin bound mesoporous structures. At the lower levels of lignin (lignin as the binder) it can be seen that from approximately 25 to 55% weight lignin there is a plateau with acceptable crush strength of ~3 Kg. Below 25% binder the strength drops rapidly. Taking account of the pore volume loss shown in FIG. 10 it can be seen that around 25% lignin offers the best combination of the pore volume retention and strength Example 5B Production of High Lignin Content Monolithic Structures In example 5A the primary purpose of using the lignin as a binder (second phase) was to produce strong, attrition resistant, structures whilst using the minimum level of level of binder to reduce the loss in pore structure. The lignin can however be used as microporous carbon precursor in its own right. The limitation is that it tends to partially melt and foam during carbonisation, see FIG. 14. We have now surprisingly found that this foaming characteristic can be completely eliminated through the addition of small amounts of the novolac resin, either as a cured resin powder or as the uncured novolac precursor, to give strong monolithic/extruded structures without the need for complex stabilisation by pre-oxidation. FIG. 13 shows the crush strength and weight loss for the carbonised TE7/20 resin—lignin composite monoliths through to the high lignin content formulations. The weight loss is essentially independent of the lignin content confirming the similar process characteristics of the synthetic and natural phenolic resins. The drop in strength at 80% lignin and higher is due to the foaming characteristic of the lignin during pyrolysis. The structure of a monolith made from 100% lignin after pyrolysis is shown in FIG. 14. It is clear that it is possible to make monoliths comprising almost entirely lignin as the precursor in the range 70-80% lignin.

Example 6

Production of Monolithic Structures Using Lignin as the Second Phase and Natural Precursors as the First Phase Monolithic carbon structures have been produced using lignin as the second phase and milled natural precursors as the first phase. Three materials have been evaluated as the first phase—rice husks, hemp shives and flax waste although the methods are equally applicable to other first phase materials.

a) Rice Husks

Rice husks were thoroughly dried and were then milled in a vibratory ball mill to produce a fine powder. This was sieved in an ultrasonic sieve to produce three fractions, <63 µm, 63-90 and >90 µm. Only the two smaller fractions were used as the larger fraction give rise to problems in the extrusion dies. A detailed examination of the paste formulation gave a mixture comprising:—

| | |
|---|---|
| Rice husk | 1000 g |
| Lignin | 334 gm |
| Methocell | 289 g |
| Polyethylene oxide | 28 g |
| Water | 1186 g |
| Other additives | 61 g |

The components were mixed in a z-blade mixer for 45 minutes. The viscoelastic dough that was formed was then extruded to produce 650 cells/square inch (CPI) monoliths After drying the monoliths were carbonised in flowing carbon dioxide. The furnace was ramped from ambient to 700° C. at 1 C/minute and held for 10 minutes before cooling. As the feed rice husk contains a significant level of silica this rises during pyrolysis to give a carbonised product containing ~40% silica. This can then be removed if required depending on the final applications. It can in principle be removed before or after activation by extraction with sodium hydroxide but if the monolith is to be activated it is preferably removed after activation as residual sodium catalyses the activation process and can cause problems. It can be removed by soaking the activated monolith in 1M NaOH solution for 5 Hr at 80° C. rinsing with water and then repeating the extraction step. After the second stage the monolith is thoroughly washed to remove any residual sodium hydroxide or sodium silicate and then with 0.5M HCl followed by further water washing. The monoliths were then thoroughly dried. After this process there was approx. 3% residual silica in the monoliths.

The pore structure properties of the materials are summarised in Table 2 with the nitrogen adsorption isotherms in FIG. 19. It can be seen that the materials that were carbonised, activated and then washed have the highest surface area.

TABLE 2

Surface Areas of Lignin bound Rice Husk Monoliths

| Monolith | Sample Code | BET $m^2/g$ | Langmiur $m^2/g$ |
|---|---|---|---|
| c | 214jun59 | 375 | 493 |
| cw | 214may32 | 830 | 1250 |
| cw | 214may31 | 824 | 1248 |
| cw | 214may33 | 800 | 1215 |
| caw | 214jul12 | 963 | 1307 |
| caw | 214jul13 | 989 | 1310 |
| c | | carbonised | |
| cw | | carbonised and washed | |
| caw | | carbonixed actifated and washed | |

The effect of removing the silica and activation on the pore volume can be seen in the following table where this has increased from 0.15 $cm^3/g$ to ~0.62 $cm^3/g$ for the carbonised and washed but with a slightly lower pore volume for the activated and then washed sample.

The pore structures of the different materials are shown in FIG. 19.

b) Hemp Shives

As received hemp shives may be processed as described above.

Example 7

Production of Controlled Meso/Macro Pore Structure Beads Using Novolac Resin-Organosolv Lignin Mixtures

Example 7(a) (Reference)

Production of/Pure Novolac Resin Derived Beads

Bead materials were produced by the method described in WO 02/12380 where the resin components (novolac and HMTA), dissolved in ethylene glycol at ~100° C., are added to mineral oil at 150° C. in the presence of a dispersant. The mixture is mechanically stirred using a paddle stirrer and the size of the beads is primarily controlled by the stirrer rotation speed. After addition of the resin/glycol solution the temperature drops and the mixture is reheated to 150° C. to complete the bead cure. The beads are then filtered from the oil and thoroughly washed in hot water to remove the EG pore former. After drying the beads were carbonised in flowing carbon dioxide at 800° C.

The meso-macro pore structure of these carbons is controlled by the ratio of the total resin solids (novolac resin plus HMTA) to ethylene glycol. The compositions are shown in the table below. As discussed above the mass of novolac and HMTA is kept constant and only the mass of ethylene glycol (EG) is varied. In the case of the Novolac resin J1098F the composition varies between E3 and E6. The table also shows the nitrogen adsorption characteristics of these materials. It can be seen that the density of the J1098F based carbon decreases steadily as the EG content is increased reflecting the increased meso/macro pore volume. Across this range the BET area, which is predominantly present in the micropores remains essentially unchanged. At even higher EG levels (TE7 and TE9) but using a different feed resin (TPR210) the bulk density drops still further.

TABLE 3

Production and Properties of meso/macro porous beads

| sample Code | Novolak | OSL | Hex | EG | BET $m2/g$ | V(0.99) $cm3/g$ | B Density $g/cm3$ |
|---|---|---|---|---|---|---|---|
| S-250-500 J1089F E3/20 | 100 | 0 | 20 | 180 | 682 | 0.62 | 0.48 |
| S-250-500 J1089F E4/21 | 100 | 0 | 20 | 210 | 631 | 1.11 | 0.44 |
| S-250-500 J1089F E5/22 | 100 | 0 | 20 | 240 | 652 | 1.06 | 0.43 |
| S-250-500 J1089F E6/23 | 100 | 0 | 20 | 270 | 631 | 1.11 | 0.35 |
| S-125-250 TE7/20 | 100 | | 20 | 300 | 556 | 0.75 | 0.28 |
| S-250-500-- TE9/16 | 100 | | 20 | 360 | 549 | 0.83 | 0.24 |

The pore structures of the J1098F derived carbons are shown in FIG. 15 and show the steady increase in mean pore size and pore volume as the EG level is increased reaching a mean pore size of 800-900 A.

Example 7 (B)

Production of Meso Macro Pore Size Beads Using a Mixture of a Standard Novolac Resin and Organosolv Lignin According to the Invention In this instance the method of production was the same as in example 7A but the novolac resin was partially substituted by Organosolv lignin (OSL) which is also soluble in the ethylene glycol (EG) pore former.

TABLE 4

Production and Properties of Water washed Organosolv lignin modified beads

| sample Code | Novolak | OSL | Hex | EG | BET $m2/g$ | V(0.99) $cm3/g$ | B Density $g/cm3$ |
|---|---|---|---|---|---|---|---|
| S-250-500 N1 OSL 1-E3 | 50 | 50 | 20 | 180 | 607 | 0.68 | 0.37 |
| S-250-500 N2 OSL 1-E3 | 66.7 | 33.3 | 20 | 180 | 633 | 0.94 | 0.39 |
| S-250-500 N4 OSL 1-E3 | 80 | 20 | 20 | 180 | 661 | 0.74 | 0.47 |
| S-250-500 N1 OSL 1-E5 | 50 | 50 | 20 | 240 | 607 | 0.46 | 0.27 |
| S-250-500 N2 OSL 1-E5 | 66.7 | 33.3 | 20 | 240 | 658 | 0.96 | 0.29 |
| S-250-500 N4 OSL 1-E5 | 80 | 20 | 20 | 240 | 679 | 1.23 | 0.31 |

After filtration from the oil the beads are split into two fractions, the first of which is water washed 3 times with hot deionised water. The second fraction is vacuum dried at 160° C. After either washing or drying to remove the ethylene glycol pore former the porous resin is carbonised at 800° C. in flowing carbon dioxide.

Three formulations were prepared, giving 12 carbonised products depending on the procedure used for removing the ethylene glycol.
1) TOSL4=4:1 ratio of Novolac to Organosolve lignin
2) TOSL2=2:1 ratio of Novolac to Organosolve lignin
3) TOSL=1:1 ratio of Novolac to Organosolve Lignin The actual TOSL4 formulation for the preparation was 80 g Novolac 20 g OSL/20 g HMTA/180 g EG.

The pore structure of the vacuum dried beads as a function of the OSL content is shown in FIG. 16 for the lower level of ethylene glycol pore former (E3). This can be compared with the pore size distributions in the absence of OSL in FIG. 15. It is immediately apparent that the presence of even small amounts of OSL has significantly increased the pore size and that this continues to increase as the OSL content increases. Comparison of Table 3 and Table 4 shows for instance that at the E3 level, the lowest level of added ethylene glycol, the carbon density is very similar. However as the amount of OSL added is increased the density drops considerably such that for the 50% OSL carbon the density of 0.37 g/cm³ is equivalent to that of the E6 carbon with double the amount of ethylene glycol. The effect is even more dramatic for the E5 formulations. In this instance the presence of 20% OSL lowers the density compared to that of the E6 formulation in the absence of EG (0.31 vs 0.35 g/cm³). At 1:1 ratio of resin to OSL (N4) the density of the product is equivalent to an E7 formulation in the absence of OSL. What is potentially more important is the impact on pore size. Comparison of FIG. 15 and FIG. 17 shows that with the OSL modified carbons, with EG at only the E5 level, it is possible to produce carbons where the mean pore size exceeds 1400 Å even at 33% added OSL whilst at 50% added OSL the mean pore size is off scale at 1600 Å. It is also noticeable that this increased pore size is achieved without a large increase in pore volume as is the case with the pure novolac materials. This can have significant benefits as the mechanical properties of the very large pore size novolac based carbons, achieved at extremely high levels of ethylene glycol, can be seriously reduced.

The inclusion of small amounts of OSL into the standard bead production route therefore provides a cost effective and practical way of controlling the pore size without recourse to the large volumes of ethylene glycol required in the normal bead production process.

Example 8

Monolith Evaluation—Adsorption of Biological Challenges

The tests described in the following examples relate to chronic kidney disease and were carried out using a variety of monoliths with nominal diameters of 7 mm, 18 mm and 28.5 mm, flow rates and reservoir capacities which are summarised below. The monolith geometry is shown schematically in FIG. 18 There are two key parameters in any calculation, the unit cell shown in FIG. 18(B) and the wall thickness shown in FIG. 18(A). The unit cell size is defined by S=W+T, which is sum of channel size, W, and wall thickness T. As long as the ratio of W:T is kept constant the overall cell size can be changed at will and in these studies was either ~600 or 1300 cells per square inch (cpi). The wall thickness (t) is independent of the cell geometry and is a function of the extrusion requirements. The varying impact of the wall is apparent from the shadowgraphs in FIG. 19 and gives rise to the variations in open area shown in Table 5.

TABLE 5

Monolith Flow Characteristics

| Monolith Geometry | | | | | Nominal | | | | | | | |
|---|---|---|---|---|---|---|---|---|---|---|---|---|
| Diameter | Length | | % open area | Free Volume | Cell Density cells/sq.in | | Flow Rate | Reservoir | cycle time | Ncycle 100 | Residence time | Linear Velocity |
| cm | cm | cpi | | cm3 | 600 | 1300 | ml/min | capacity ml | min | mins. | time mins | cm.sec |
| 0.7 | 9.5 | 600 | 11.5 | 0.4 | blood | | 5 | 20 | 4 | 25 | 0.08 | 0.22 |
| 0.7 | 9.5 | 1300 | 14.6 | 0.5 | | plasma | 5 | 20 | 4 | 25 | 0.11 | 0.22 |
| 1.8 | 28.5 | 600 | 33.2 | 24.1 | plasma | | 300 | 400 | 1.3 | 75.0 | 0.08 | 1.96 |
| 2.85 | 22.5 | 600 | 33.2 | 47.7 | blood plasma | | 300 | 400 | 1.3 | 75.0 | 0.16 | 0.78 |

In all of these tests the feed was continuously withdrawn from the monolith assembly via the sealed feed reservoir from where it passed back to the monolithic adsorber via a peristaltic pump. Analysis was carried out by sampling from the stream before it passed back to the monolith (FIG. 20). Under this method of operation, using either blood or plasma, the time taken to pass the entire reservoir contents through the monolith is a function of the reservoir capacity and the flow rate. This cycle time is also shown in the table and varies between 4 min for the smallest monolith and 1.3 min for the 20 and 30 mm monoliths. In general, the experiments were continued for around 100 minutes so that the number of times the feed was cycled through the monolith varies between 25 and 75. These conditions can be compared to conventional dialysis conditions where the flow rate is usually 300 ml/min but the blood reservoir in an adult is 5-7 L. This would give a cycle time of 20 minutes and 15 cycles in a normal dialysis period of 3 hours, considerably lower than in any of the tests. This makes a direct comparison of the performance of the different monoliths and extrapolation to a real dialysis system difficult.

Whilst the majority of the test data is presented based on direct measurements of concentration vs time, the results have also been normalised by determining the challenge removal and weight uptake on the carbon as a function of the number of passes through the monolith.

a) Removal of IL-6 from Circulating Plasma

The tests were carried out using the 7 mm monoliths described in Example 5A and in table 5.

Before the experiment, monoliths were connected to a multi-channel peristaltic pump, and washed by circulating 20 ml of PBS at the flow rate of 5 ml/min for 30 min. For each monolith, 20 ml of plasma spiked with 1000 pg/ml IL-6 were circulated through at the flow rate of 5 ml/min. Plasma samples were collected after 5, 30, 60 and 120 min of circulation. The remaining IL-6 concentrations were determined by ELISA assay, performed following manufacturer's instructions. The results are shown in FIG. 21. Among all the tested monoliths, TE7/Lignin 50/50 sample showed least removal of IL-6, while TE7/Lignin 90/10 showed best IL-6 removal. However, the optimal monoliths require both biotoxin removal and mechanical strength, TE7/Lignin 75/25 gave the required combination of properties.

b) IS and PCS Removal by Monoliths with Increasing Lignin Content

All the tested 7 mm monoliths showed efficient removal of the albumin bound liver toxins, IS (FIG. 22) and PCS (FIG. 23) during 120 mins of plasma circulation. However, the TE7/Lignin (50:50) monoliths showed slower removal of both IS and PCS demonstrating some degree of blocking of the pore structure. Plasma samples passed through all tested monoliths showed significant reduction ($p>005$) of IS and PCS compared to the control. There was no significant difference ($p>0.05$) in IS removal among all tested monoliths except the TE7/Lignin 50/50 at 5 min time point ($<0.001$). There was no significant difference ($p>0.05$) in PCS removal among monoliths TE7/Resin 50/50, TE7/Lignin 75/25 and TE7/Lignin 90/10 after 5, 30, 60 and 120 mins of plasma circulation. Although plasma PCS concentration after circulation through TE7/Lignin 50/50 at 5 and 30 min was significantly higher ($<0.001$) than the rest of the monoliths, no significant difference was observed after 60 and 120 minutes of circulation.

(c) Normalised Adsorption of IL-6 from Spiked Human Plasma Using 7 mm, 18 mm and 28 mm Monoliths with Varying CPI The details of the monoliths used are shown in Table 6 along with the weight uptake per gm of carbon in the monoliths and the % removal from the feed stream after 15 passes for three challenges IL6, PCS and IS. The samples numbers refer to the different monoliths used in these tests. These were all produced with 25% weight lignin binder. The cyclic adsorption over the complete adsorption cycle is shown in FIG. 24 for the adsorption of IL6, FIG. 25 for PCS and FIG. 26 for IS.

(d) Evaluation of Adsorption from Whole Blood Using 28.5 mm Diameter Monoliths

The 25 cm×~30 mm OD monoliths derived from 25 wt % lignin and 75 wt % TE7 resin prepared as in Examples 2 and 3 were mounted into the ends of large plastic syringes and sealed in place with shrink wrap tubing. This can be seen to the side of the pump system in FIG. 20. The monolith testing was carried out using both plasma and healthy donor whole bloods (400 ml from each donor) with sodium heparin anticoagulation purchased from Cambridge Bioscience Ltd (UK). These were then dosed with the challenge molecules. The feed solution, blood or plasma, was continuously recycled from the reservoir through the column at 300 ml/minute.

The results for adsorption from plasma for IL6 and TNFα are shown in FIG. 27 and the removal of and IS and PCS from plasma in the 30 mm monoliths PCS in FIG. 28. The reduced rate of adsorption for the larger molecules is clearly shown. The adsorption of these molecules IS, PCS, IL6 and TNFα from whole blood are shown in FIG. 29. Comparison of FIG. 27 and FIG. 28 in plasma and FIG. 29 in whole blood shows that the adsorption from plasma and whole blood is very similar.

Example 9

Monolith Evaluation—Adsorption of Biological Challenges Treatment of Alcohol Poisoning a) Monolith Production The monoliths were extruded using a 42 mm die with a nominal 600 cpi cell density as described in example 5A After drying the monolith was carbonised at 750 C in flowing carbon dioxide and then activated at 850 C in flowing carbon dioxide.

TABLE 6

| | Die size (mm) | (cpi) | Weight (g) | Length (cm) | Diameter (cm) | Open Channel area (%) | Number of Channels |
|---|---|---|---|---|---|---|---|
| #1 | 10 | 1300 | 1 | 9.5 | 0.7 | 12.2 | 71 |
| #2 | 10 | 600 | 1 | 9.5 | 0.7 | 11.8 | 25 |
| #3 | 20 | 600 | 15 | 20 | 1.8 | 29.5 | 240 |
| #4 | 30 | 600 | 44 | 21 | 2.8 | 33.2 | 544 |

| | IL-6 removal @ 15 passes | | PC removal @ 15 passes | | IS removal @ 15 passes | |
|---|---|---|---|---|---|---|
| | % removal | Adsorption (ng/g) | % removal | Adsorption (µmol/g) | % removal | Adsorption (µmol/g) |
| #1 | 86 ± 9 | 9.9 ± 1.0 | 99* ± 2 | 7.2* ± 0.1 | 100* ± 0 | 2.4* ± 0.0 |
| #2 | 60 ± 10 | 5.4 ± 0.9 | 92 ± 3 | 5.9 ± 1.0 | 90 ± 5 | 1.9* ± 0.9 |
| #3 | 16 ± 1 | 6.4 ± 0.7 | 40 ± 7 | 5.6 ± 0.2 | 40 ± 10 | 2.8 ± 0.2 |
| #4 | 54 ± 7 | 6.0 ± 2.0 | 67 ± 10 | 1.4 ± 0.2 | 78 ± 11 | 0.8 ± 0.1 |

PCS and IS are both small molecules that can absorb in the micropore structure of the carbons. However, these results show that despite the small molecular size there is a marked difference in performance of the different structure monoliths. The rate of adsorption or removal is maximised for the smallest, 7 mm, monoliths. The kinetics of both the 18 and 28 mm monoliths is significantly reduced. This difference in rate is also apparent for IL6 (FIG. 24). However, in this case there is a significant improvement in performance with the higher cell density monolith. These results indicate that improved performance should also be expected for the larger monoliths at higher cell densities particularly for the larger challenge molecules.

b) Adsorption from Donor Blood—In Vitro Experiments

The donor blood was spiked with 5 mL of 33% ethanol per blood container (approximately 380 mL). An erythrocyte suspension was used as donor blood, which was leucocvte-free.

The 'haemoperfusion' (HP) session was run for 60 minutes using the standard dialysis equipment at flow rate 140 mL/min (Fresenius). 22-24 mm diameter carbon monoliths were used as described in (a). The results are shown in Table. (n=10)

TABLE 7

Alcohol adsorption by monolithic carbon from donor blood spiked with alcohol

| Alcohol content in blood after spiking at t = 0 (‰) | Alcohol content in blood after 60-min HP, (‰) | Amount of alcohol adsorbed, mg | Monolith adsorption capacity, mg/g | Degree of alcohol removal, % |
|---|---|---|---|---|
| 2.54 ± 0.04 | 0.82 ± 0.06 | 532.6 ± 13.8 | 21.3 ± 0.4 | 67.5 ± 0.6 |

The biochemical parameters of blood remained unaffected by haemoperfusion over the carbon monolith.

It can be seen that from the initial high blood alcohol level approaching 70% of the alcohol was removed in 60 minute haemoperfusion period, sufficient to reduce the blood alcohol level from a dangerously high level to a safe level.

c) In Vivo Experiments Using Animals

Mongrel dogs (n=30), 10-14 kg weight, were injected with 60 mL of 33% alcohol to induce alcohol intoxication.

The haemoperfusion session was run for 60 minutes using the standard dialysis equipment at flow rate 140 mL/min (Fresenius dialysis system). The tests were carried out using the carbon monoliths, diameter 22-24 mm, described in (a). The results are shown in Table. It can be seen that the monoliths were effective at significantly lowering the blood alcohol and that nearly all the observed alcohol removal took place in the first 30 minutes.

TABLE 8

Alcohol concentration in the animal blood before and during HP

| Time, min | Alcohol content in blood, ‰ | Degree of alcohol removal, % |
|---|---|---|
| Before injection | — | — |
| 0 (immediately after injection) | 3.04 | 0 |
| 30 min of HP | 1.31 | 57 |
| 60 min of HP | 1.24 | 60 |

Example 10

Monolith Evaluation—Adsorption of Biological Challenges Reduction in Thrombosis Using Monolithic Vs Granular Carbon One group of dogs (n=10) was treated with haemoperfusion (HP) without heparin injection. In HP through granulated carbon (Gambro, Sweden and Omsk, Russia) the thrombosis was observed after 10-12 min, whereas in HP through the monoliths thrombosis occurred after 20-25 min.

The other group of dogs (n=20) was treated with HP with heparin injection, 5000 units for HP over granulated carbon and 2,500 units for HP over monolith carbon. The biochemical parameters of blood remained unaffected by haemoperfusion over the carbon monolith.

This clearly demonstrates the benefit of using the monolithic carbon in allowing a significant reduction in heparin use during haemoperfusion.

Example 11

Treatment of Sepsis and SIRS

This relates to two types of problem. SIRS (systemic inflammatory response syndrome) is an inflammatory state affecting the whole body that isn't always connected with a bacterial infection whilst Sepsis is defined as SIRS and an associated diagnosed infection. In both cases removal of the inflammatory cytokines is required but in the case of Sepsis the removal of the infective agent, represented in these tests by Staphylococcal enterotoxin B (SEB) is also required.

Adsorption studies were carried out by incubation of the microporous/mesoporous carbon beads in human plasma spiked with Staphylococcal enterotoxin B (SEB) and adsorption over time was measured by enzyme linked immunosorbent assay (ELISA). SEB adsorption by carbon beads was found to be linked to the controlled porosity whereby, carbon 9 (meso/macroporous) removed significantly more SEB than both carbon 5 (2-30 nm pores) and carbon 1 (microporous) (p<0.01, n=3 FIG. 28). The porosity of bead carbon 9 is essentially the same as the porosity of the monolithic carbons of the present invention. As it has been demonstrated that the monolithic carbon is capable of removing the cytokine TNFα from both flowing blood (FIG. 29) and flowing plasma (FIG. 27) it is reasonable to assume that the SEB would also be removed using monoliths in place of beads in a haemoperfusion application.

Example 12

Treatment of Acute-On-Chronic Liver Failure ACLF

Acute-on Chronic liver disease (ACLF) is characterised by a rapid loss of function in up to 90% of a patients liver cells. Extracorporeal liver support is targeted at the detoxification of patient blood as a bridge to transplantation. This requires the removal of a wide range of both small molecule toxins and albumin bound toxins such as phenol, tryptophan, cholic acid and bilirubin.

a) Evaluation Using Bead Form Carbons

The bead form carbons used in these tests are summarised in Table 7

TABLE 7

Bead for carbon properties used in the liver failure tests

| | d (nm) | D (g/ml) | $V_{micro}$ (cm$^3$/g) | $V_{micro}$ (cm$^3$/ml) | $S_{BET}$ (m$^2$/g) | $S_{BET}$ (m$^2$/ml) |
|---|---|---|---|---|---|---|
| A1 | <2 nm | 0.56 | 0.69 | 0.39 | 1204 | 674 |
| A2 | 30 | 0.38 | 1.30 | 0.49 | 1559 | 592 |
| A3 | 70 | 0.27 | 1.75 | 0.47 | 1493 | 403 |
| A4 | 80 | 0.21 | 1.80 | 0.38 | 1548 | 325 |
| A5 | 120 | 0.18 | 1.61 | 0.29 | 1235 | 222 |

The beads were incubated with 5.4 ml of fresh human plasma spiked with 2 μmol/ml of phenol, 0.1 μmol/ml of tryptophan or cholic acid or 0.3 μmol/ml of bilirubin. 0.6 ml samples were collected at 5, 15, 30 and 60 minutes and were analysed using standard test methods. Tests were carried out using 5 replicates.

The removal of the lower binding energy toxins (phenol, tryptophan and cholic acid) was complete in 10 minutes for all of the carbons tested (e.g FIG. 31—tryptophan) whereas the adsorption of bilirubin the highest binding energy molecule, only took place by the larger pore carbons (A4 and A5) and required 60 minutes to reach equilibrium (FIG. 32)

A detailed examination of these results shows that the overall performance is a complex balance between the strength of adsorption of the unbound molecule on carbon, the strength of the albumin-molecule binding and the nature of the pore structure.

b) In-Vivo Evaluation Using Monolithic Carbons.

These in-vivo tests were carried out using male Sprague-Dorley rats (250-300 g) where half of the animals underwent bile duct ligation (BDL) to induce liver failure. After 28 days the animals were connected to an extracorporeal circuit using a carbon monolith for 3 hours. Blood samples, blood pressure and body temperature were taken hourly.

The monoliths used in the tests were 7 mm diameter, 95 mm long, 25% weight lignin bound 600 cpi meso/macro porous monoliths as described in Example 5A. The monoliths had a bimodal pore structure with 1 nm micropores and ~80 nm macropores. This is identical to the A4 bead carbons used in (a).

The only significant change in the observed results for the BDL and sham animals was the bilirubin content of the blood. FIG. 33 shows that in agreement with the bead test data using spiked plasma, there is a steady reduction in the bilirubin content of the blood over the course of the 3 hour perfusion test. As bilirubin is the most difficult of the liver toxins to remove this clearly shows that the more easily adsorbed liver toxins should be easily removed from circulating blood using the macroporous monoliths.

The invention claimed is:

1. A method for producing a carbonised and optionally activated monolith structure from a first component which is particles of a fully cured phenolic novolak resin exhibiting mesoporosity with mesopores of diameter 2-50 nm and 10-40% by weight of a second component which is high purity water insoluble powdered lignin, said method comprising:
mixing the first and second components;
producing an uncarbonised monolith structure from the mixture by extrusion or pressurised moulding; and
forming from the uncarbonized monolith structure a carbonised and optionally activated monolith structure comprising micro-meso porous carbon particles exhibiting microporosity and retained mesoporosity and bound with carbonised lignin, the carbonised monolith exhibiting micropores of diameter <2 nm, mesopores of diameter 2-50 nm and voids of size >1 μm between the particles defining paths for fluid to flow into and through the structure.

2. The method of claim 1; having one or more of the following features:
(i) forming a dough by mixing the lignin component with milled particles of the phenolic resin novolak component and optionally other additives to control the rheology the dough;
(ii) extruding the dough to form a shaped body having walls defining a multiplicity of internal channels for fluid flow, the channels being directed along the extrusion direction;
(iii) the shaped body is a structure having walls defining a multiplicity of internal transport channels for fluid flow the transport channels being directed along the extrusion direction;
(iv) carbonising the extruded structure at a temperature of at least 700° C. in an inert gas;
(v) activating the carbonised extruded structure by treating in flowing carbon dioxide at a temperature of at least 850° C. for a time selected to give a required weight loss of at least 20%.

3. The method of claim 1, for producing said shaped forms in either bead or granular form, and including the steps of: (a) dissolving a water insoluble lignin and novolac resin in ethylene glycol; (b) dissolving hexamethylenetetramine (HMTA) curing agent in ethylene glycol; (c) mixing the two solutions to give at least 15 parts of HMT per 100 parts of resin solids (lignin+novolac), the ratio of the total solids (lignin+novolac+HMT) to ethylene glycol and of lignin to novolac being selected according to the required macroporosity.

4. The method of claim 3, wherein the mixed solution is poured into a tray, cured at 150° C. for 2 hours and then comminuted to form powder.

5. The method of claim 1, which comprises:
(i) providing solid particles of a pure water insoluble lignin powder and mixing these with particles of a cured meso/macro porous phenolic resin;
(ii) forming the mixture into a dough; and
(iii) extruding the dough to form a shaped product.

6. The method of claim 5, having any of the following features:
(i) the dough is extruded to form a shaped body having walls defining a multiplicity of internal channels for fluid flow; the channels being directed along the extrusion direction;
(ii) the shaped body is a square channel monolith of 100-1000 μm cell dimension and cell walls with thickness 100-1000 μm;
(iii) the cell density is at least 600 channels per square inch;
(iv) the cell density is at least 1000 channels per square inch;
(v) carbonising the extruded structure;
(vi) activating the carbonised extruded structure by treating in flowing carbon dioxide at a temperature of at least 850° C. for a time selected to give a required weight loss of which may be at least 20%, preferably 25%;
(vii) lignin is a product of the Organosolv process;
(viii) the particles of lignin have a D90 of less than 100p and a mean particle size of approximately 40 μm;
(ix) the content of the lignin component is 10-40% weight;
(x) the content of the lignin component is about 25% weight;
(xi) the meso/macroporous resin is formed by:
(a) providing a nucleophilic component which comprises a phenolic compound or a phenol condensation prepolymer;
(b) dissolving the nucleophilic component in a pore former selected from the group consisting of a diol, a diol ether, a cyclic ester, a substituted cyclic ester, a substituted linear amide, a substituted cyclic amide, an amino alcohol and a mixture of any of the above with water, together with at least one electrophilic cross-linking agent selected from the group consisting of formaldehyde, paraformaldehyde, furfural and hexamethylenetetramine (HMTA);
(c) condensing the nucleophilic component and the electrophilic cross-linking agent in the presence of the pore former to form a porous resin; and
(d) comminuting the porous resin;
(xii) the nucleophilic component is a phenol formaldehyde novolac, the pore former is ethylene glycol and the curing agent is HMTA;

(xiii) the novolac HMTA curing agent are dissolved in ethylene glycol (EG) to give a ratio of solids (Novolac+HMTA) to EG selected to give the required meso/macro pore structure and a solids composition comprising at least 15 parts weight HMT and 100 parts novolac;

(xiv) a block of cured resin is granulated to give particles of approximately 1 mm, after which the ethylene glycol is removed from the granulated cured resin by either washing in hot water or vacuum drying;

(xv) the ethylene glycol-free granulated resin is jet milled to provide a powder with at least 90% of the powder <100 μm;

(xvi) the particles of phenolic resin have a mean particle size of approximately 40 μm;

(xvii) forming the dough by mixing the first lignin component with the milled resin particles and with methyl cellulose, PEO and water;

(xviii) the second, naturally occurring component has a D90 of <100 mirons and mean particle size of approximately 40 μm;

(xix) forming the dough by mixing the first lignin component with the milled particles of the second component and optionally other additives to control the rheology the dough.

* * * * *